(12) United States Patent
Spanova et al.

(10) Patent No.: US 10,231,985 B2
(45) Date of Patent: Mar. 19, 2019

(54) COMPOUNDS AND COMPOSITIONS COMPRISING SUCH COMPOUNDS FOR THE PREVENTION OR TREATMENT OF DYSLIPIDAEMIAS

(71) Applicants: CENTRE NATIONAL DE LA RECHERCHE SCIENTIFIQUE, Paris (FR); UNIVERSITE DE POITIERS, Poitiers (FR); UNIVERSITY OF EXETER, Exeter, Devon (GB)

(72) Inventors: Miroslava Spanova, Tlmace-Lipnik (SK); Thierry Ferreira, Iteuil (FR); Romain Clement, Poitiers (FR); Shalinee Dhayal, Saltash Cornwall (GB); Noël Morgan, Gunnislake Cornwall (GB)

(73) Assignees: CENTRE NATIONAL DE LA RECHERCHE SCIENTIFIQUE, Paris (FR); UNIVERSITE DE POITIERS, Poitiers (FR); UNIVERSITY OF EXETER, Exeter Devon (GB)

( * ) Notice: Subject to any disclaimer, the term of this patent is extended or adjusted under 35 U.S.C. 154(b) by 39 days.

(21) Appl. No.: 15/028,139

(22) PCT Filed: Oct. 8, 2014

(86) PCT No.: PCT/FR2014/052546
§ 371 (c)(1),
(2) Date: Apr. 8, 2016

(87) PCT Pub. No.: WO2015/052433
PCT Pub. Date: Apr. 16, 2015

(65) Prior Publication Data
US 2016/0256429 A1    Sep. 8, 2016

(30) Foreign Application Priority Data

Oct. 8, 2013  (FR) ..................................... 13 02334

(51) Int. Cl.
| | | |
|---|---|---|
| *A61K 31/231* | (2006.01) | |
| *A61K 31/357* | (2006.01) | |
| *A61K 31/7032* | (2006.01) | |
| *A61K 31/661* | (2006.01) | |
| *A61K 31/232* | (2006.01) | |
| *A61K 31/7024* | (2006.01) | |
| *A61K 31/201* | (2006.01) | |
| *A61K 45/06* | (2006.01) | |
| *A23L 33/12* | (2016.01) | |
| *A61K 31/164* | (2006.01) | |

(52) U.S. Cl.
CPC .......... *A61K 31/7024* (2013.01); *A23L 33/12* (2016.08); *A61K 31/164* (2013.01); *A61K 31/201* (2013.01); *A61K 31/231* (2013.01); *A61K 31/232* (2013.01); *A61K 31/357* (2013.01); *A61K 31/661* (2013.01); *A61K 31/7032* (2013.01); *A61K 45/06* (2013.01); *A23V 2002/00* (2013.01)

(58) Field of Classification Search
CPC .. A61K 31/231; A61K 31/661; A61K 31/232; A61K 45/06; A61K 31/7032; A61K 31/357
USPC .......................................................... 514/23
See application file for complete search history.

(56) References Cited

U.S. PATENT DOCUMENTS 7,700,583 B2 * 4/2010 Gundertofte ........... A61K 31/16
                                                        514/213.01

FOREIGN PATENT DOCUMENTS

| EP | 0 104 043 | 9/1983 |
|---|---|---|
| WO | WO 01/17472 | 3/2001 |
| WO | WO 02/083059 | 10/2002 |
| WO | WO 03/040354 | 5/2003 |
| WO | WO 2010/149170 | 12/2010 |
| WO | WO 2012/054527 | 4/2012 |

OTHER PUBLICATIONS

Evans et al. Fate of Mannide Monooleate in the Animal Body. Proceedings of the Society for Experimental Biology and Medicine. Nov. 1942;51(2):222-223.*
Glossary of medical education terms, Institute of International Medical Education. http://www.iime.org/glossary.htm Accessed in Mar. 2013. (Year: 2013).*
Schwab et al. Effect of the amount and type of dietary fat on cardiometabolic risk factors and risk of developing type 2 diabetes, cardiovascular diseases, and cancer: a systematic review. Food & Nutrition Research 2014, 58: 25145, http://dx.doi.org/10.3402/fnr.v58.25145 (Year: 2014).*
Guy et al. Lipid and Lipoprotein Profiles in Youth With and Without Type 1 Diabetes. Diabetes Care 32:416-420, 2009. (Year: 2009).*

(Continued)

*Primary Examiner* — Yih-Horng Shiao
(74) *Attorney, Agent, or Firm* — Saliwanchik, Lloyd & Eisenschenk

(57) ABSTRACT

The present invention relates to the field of medicine. It more particularly relates to the use of compounds for preventing and/or treating dyslipidemia in a subject, said dyslipidemia typically being linked to the excess presence in the biological membranes, including in the biological membranes of non-adipocyte cells, of fatty acids, in particular of saturated long-chain fatty acids, and/or of sterols. The invention also relates to compositions, in particular pharmaceutical compositions and food supplements or complements, comprising such compounds, and to the uses thereof for preventing and/or treating dyslipidemia. The compounds and compositions according to the invention can in particular be advantageously used for preventing and/or treating a pathological condition selected from metabolic syndrome and/or a symptom or abnormality characteristic of metabolic syndrome, preferably for preventing or treating type 2 diabetes mellitus or hepatic steatosis.

7 Claims, 10 Drawing Sheets

(56) References Cited

OTHER PUBLICATIONS

Figure 1:
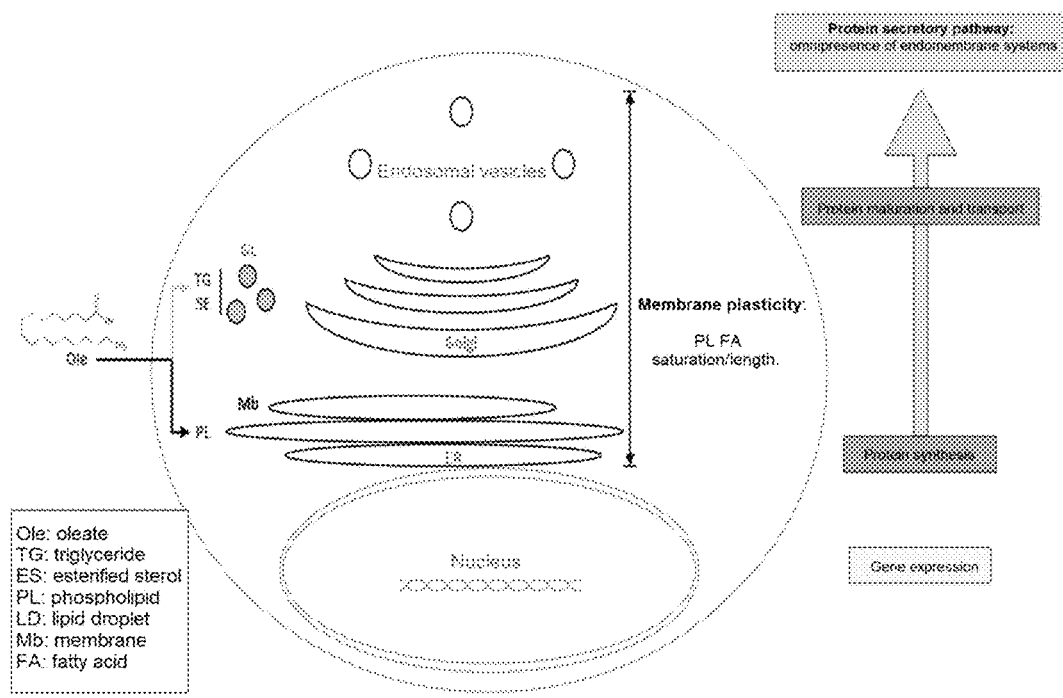

Davis et al. Islet autoantibodies in clinically diagnosed type 2 diabetes: prevalence and relationship with metabolic control (UKPDS 70).Diabetologia (2005) 48: 695-702. (Year: 2005).*
Morgan, N. G. et al. "Unsaturated fatty acids as cytoprotective agents in the pancreatic β-cell" *Prostaglandins, Leukotrienes and Essential Fatty Acids*, Apr. 1, 2010, pp. 231-236, vol. 82, Nos. 4-6.
Payet, L.-A. et al. "Saturated Fatty Acids Alter the Late Secretory Pathway by Modulating Membrane Properties" *Traffic*, Dec. 2, 2013, pp. 1228-1241, vol. 14, No. 12.
Payet, L.-A. "Effets des acides gras saturés sur la voie de sécrétion. Relation avec la mucoviscidose" *Thèse Université de Poitiers*, Nov. 29, 2013, pp. 1-197, XP-055159587, retrieved from Internet: http://nuxeo.edel.univ-poitiers.fr/nuxeo/site/esupversions/e25b5dd2-e52f-4642-a645-072e90abd59d.
Pineau, L. et al. "Lipid-Induced ER Stress: Synergistic Effects of Sterols and Saturated Fatty Acids" *Traffic*, Jun. 2009, pp. 673-690, vol. 10, No. 6.
Stone, V. M. et al. "The cytoprotective effects of oleoylethanolamide in insulin-secreting cells do not require activation of GPR119", Apr. 2012, pp. 2758-2770, vol. 165, No. 8.
Written Opinion in International Application No. PCT/FR2014/052546, Jan. 15, 2015, pp. 1-9.

* cited by examiner

COMPOUNDS AND COMPOSITIONS COMPRISING SUCH COMPOUNDS FOR THE PREVENTION OR TREATMENT OF DYSLIPIDAEMIAS

CROSS-REFERENCE TO RELATED APPLICATION

This application is the U.S. national stage application of International Patent Application No. PCT/FR2014/052546, filed Oct. 8, 2014.

The present invention relates to the field of medicine. It relates more particularly to the use of compounds for preventing and/or treating dyslipidemia in a subject, whether said dyslipidemia is of food origin or, alternatively, is cellular hypoxia-related, said dyslipidemia typically being linked to the excess presence in the biological membranes, including in the biological membranes of non-adipocyte cells, of fatty acids, in particular of saturated long-chain fatty acids, and/or of sterols. The invention also relates to compositions, in particular pharmaceutical compositions and food supplements or complements, comprising such compounds, and to the uses thereof for preventing and/or treating dyslipidemia. The compounds and compositions according to the invention can in particular be advantageously used for preventing and/or treating a pathological condition selected from metabolic syndrome and/or a symptom or abnormality characteristic of metabolic syndrome, preferably for preventing and/or treating type 2 diabetes mellitus (T2DM) or hepatic steatosis.

PRIOR ART

Insulin resistance, insulin deficiency, hyperglycemia, hypercholesterolemia, in particular hypercholesterolemia characterized by a low HDL cholesterol concentration, hypertriglyceridemia, hypertension, heart failure and hepatic steatosis are among the symptoms or anomalies characteristic of metabolic syndrome.

Metabolic syndrome is defined in particular and typically (in the absence of treatment) as the appearance of at least three of the following five anomalies: abdominal obesity, hypertriglyceridemia (TG≥about 1.7 mM), low HDL cholesterol concentration (HDLc<about 1 mM for men and <about 1.3 mM for women), hypertension (BP≥about 130/85 mm Hg) and fasting blood sugar≥about 5.5 mM (see "Syndrome métabolique et diabète chez l'homme. Composition lipidique et oxidation des lipoprotéines de basse densité (DL) plasmatiques en relation avec l'activation des plaquettes sanguines," thesis manuscript of Romain Colas, defended on 10 Dec. 2010). The involvement of dyslipidemias in the development of metabolic syndrome has been known for several decades.

Dyslipidemia is typically defined as an abnormally high or low blood concentration of lipids, typically of free or non-esterified fatty acids, of sterols (for example cholesterol), of triglycerides or of phospholipids. Most dyslipidemias consist of an increase in the level of these elements, a decrease being much rarer.

Non-esterified fatty acids (NEFA) or free fatty acids (FFA) are an important energy component of the organism. They consist of a complex mixture of fatty acids differing in their number of double bonds and the number of carbon atoms making up their hydrocarbon chain. Of endogenous origin, they are formed by biosynthesis in the cell cytoplasm and are used for the synthesis of triglycerides, in the form of acyl-CoA, in the adipose tissue and the liver, or are oxidized by cells. They also enter the composition of the structural lipids making up the biological membranes, such as phospholipids and sphingolipids. In the plasma, chiefly four fatty acids, accounting for 85% of the NEFA, are found: oleic, palmitic, linoleic and stearic acids. Most NEFA are bound to albumin. They come from adipose tissue triglycerides hydrolyzed during fasting, under the action of lipoprotein lipase in the tissues and blood, to glycerol and fatty acids. Their concentration varies in large proportions according to age, food intake and physical exercise. Generally, in the postprandial period, their release is suppressed.

A sterol is a lipid having a sterane core, the carbon 3 of which bears a hydroxyl group. Sterols are regarded as a subclass of steroids. Cholesterol, one of the most common and widespread sterols, is vital for cellular functioning and is a precursor of vitamins and of liposoluble steroid hormones.

Typically, an abnormally high concentration of lipids in the blood corresponds to an abnormally high concentration of lipids in the biological membranes ("cellular dyslipidemia"). For example, an abnormally high concentration of saturated free fatty acids (NEFA) in the blood corresponds to an abnormally high concentration of saturated esterified fatty acids (EFA) in the phospholipids of the biological membranes. These lipids are always found associated with specific proteins in order to form lipoproteins. Dyslipidemias result from a dysregulation of lipid homeostasis.

It is established that a diet excessively rich in animal fats leads in particular to an accumulation of saturated fatty acids (SFA) in the biological membranes (lipointoxication) and that this leads to the global disruption of membrane plasticity at the cellular level and then to the metabolic inactivation of the cells and, in the long term, to apoptosis of the cell (FIG. 1).

Heretofore, only unsaturated fatty acids (UFA), in particular oleic acid (olive oil), were known to counter the deleterious effects of the toxicity associated with SFA accumulation (Cunha et al., 2008; Diakogiannaki et al., 2008; Katsoulieris et al., 2009; Pineau et al., 2009; Stein et al., 1997; Wei et al., 2006; Deguil et al., 2011). However, their use as a functional food and/or medicine encounters two major limits. First, UFA have essentially preventive properties and are thus of limited interest in the context of the treatment of established lipointoxications, i.e., lipointoxications responsible for a disruption of all membrane mechanisms (detectable in each step of the protein secretory pathway). Indeed, UFA act via direct competition with SFA, when food is ingested, in the synthesis of membrane phospholipids (PL). Second, UFA toxicity was shown on cells unable to transform (buffer) and then store excess free fatty acids, in particular UFA, in neutral lipids, typically in triglycerides (TG) and/or esterified sterols. That is the case, for example, for a yeast strain in which, due to the absence of the four acyltransferase enzymes Lro1p, Dga1p, Are1p and Are2p, a dysregulation of the synthesis of neutral lipids is observed. When this mutant strain is exposed to a source of exogenous UFA, lipid dysregulation is expressed as a massive proliferation of intracellular membranes and ultimately as cell death, by a process independent of the unfolded protein response (UPR; see below) (Kohlwein & Petschnigg, 2007; Petschnigg et al., 2011). Interestingly, identical phenomena could be observed in mammalian cells (Listenberger et al., 2003). This explains why unsaturated fatty acids become toxic to the cell under lipointoxication conditions prior to the latter, a state in which the cell's ability to store unsaturated fatty acids as neutral lipids is exceeded (a so-called "metabolically inactive" lipointoxicated cell), or, alternatively, under normal conditions, for cells having a very weak ability to synthesize TG, such as pancreatic non-β cells (Cnop M et al., 2001). In humans, all cell types except for adipocytes (alone able to synthesize and store neutral lipids) are thus likely to be concerned by lipointoxication. It is known in particular that disruptions linked to SFA accumulation lead to apoptosis of pancreatic β-cells responsible for insulin synthesis (Butler et al., 2003) or to that of hepatocytes (Egnatchik et al., 2014).

In the case of type 2 diabetes mellitus (T2DM), the repercussions of SFA accumulation appear in various organs and are expressed in particular by insulin deficiency in the pancreas (related to apoptosis of pancreatic β-cells, described above) and also by insulin resistance in the liver and the muscles.

It is estimated today that there are 382 million diabetic individuals worldwide. Although the involvement of lipid homeostasis dysregulation has been established for several decades, most current treatments are focused on the insulin secretion level or the blood sugar level. In concrete terms, several molecules are employed for treating type 2 diabetes mellitus. These are tested for each patient and then sequentially replaced by new ones (according to their effect on body mass and other potential side effects) if they prove ineffective. According to the 2006 recommendations of the French drug safety agency, AFSSAPS, metformin (a type of biguanide) is used first and foremost in order to decrease insulin resistance without causing hypoglycemia. Second, insulin secretion agents such as sulfonamide-based hypoglycemics or meglitinides can be used. Furthermore, since 2008, DPP-4 inhibitors (gliptins) and other GLP-1 analogs (incretin mimetics) have also appeared among the range of products available to correct glycemia without interest in the context of dyslipidemia. Finally, as a last resort, insulin injections are prescribed.

None of the strategies mentioned make it possible to fundamentally restore the functionality of lipointoxicated cells and organs, and are therefore, unable to intervene in the early steps in the cascade of deleterious effects encountered in metabolic syndrome or in type 2 diabetes mellitus, typically upstream from each step targeted by the existing treatments. The contemporary therapeutic approach which aims at stimulating the physiological functions of "sick" organs may even, counterproductively, contribute to their weakening and explain the ineffectiveness of the medicines used in many patients and, in addition, the appearance of resistance phenomena over time.

The Inventors now describe molecules or compounds, and compositions comprising such molecules or compounds, for preventing the onset of dyslipidemia in the biological membranes, typically the cellular accumulation of fatty acids, in particular of saturated fatty acids, and/or of sterols, or for treating established dyslipidemia by acting on the phenomenon commonly altered in all the lipointoxicated tissues: membrane plasticity.

SUMMARY OF THE INVENTION

The invention relates to a novel class of molecules for preventing or treating pathologies associated with lipointoxication by fatty acids, typically by saturated fatty acids (SFA) and/or by sterols, in particular by saturated long-chain and/or trans fatty acids. By long-chain fatty acids is typically meant fatty acids the carbon chain of which comprises at least 14 carbon atoms, typically between 14 and 24 carbon atoms, for example at least 16 or at least 18 carbon atoms, typically between 14 and 22 or between 14 and 18 carbon atoms.

Lipointoxication can appear as an inversion of the saturated fatty acid/unsaturated fatty acid (SFA/UFA) ratio in the phospholipids (PL) present in the biological membranes, the SFA becoming predominant, even completely replacing the UFA. The molecules of the invention are thus typically for preventing or treating dyslipidemia, metabolic syndrome, a symptom or abnormality characteristic of metabolic syndrome, preferably for preventing or treating type 2 diabetes mellitus or hepatic steatosis.

A considerable advantage of the molecules (or compounds) of the invention, compared to the unsaturated fatty acids (UFA), in particular oleic acid, used in the prior art to compensate for an excess of saturated fatty acids (SFA), is that unlike the latter, they do not cause any cellular toxicity, in particular any toxicity to cells unable to synthesize neutral lipids, typically non-adipocyte cells, for example pancreatic cells. The molecules of the invention have another major advantage in that, unlike the UFA used preventively in the prior art, they can also be used therapeutically due to their ability to restore cellular functionality, for example by acting on membrane plasticity. They can thus advantageously be used to treat established dyslipidemia, i.e., dyslipidemia responsible for a detectable cellular dysfunction, typically an alteration of the capacity, even an incapacity (metabolic inactivation), of the cell to exert its natural function.

A particular object of the invention thus relates to a compound comprising a polar head, comprising at least one hydroxyl residue, on which is grafted a single unsaturated fatty acid comprising between 16 and 24, for example between 16 and 22 or 16 and 20, carbon atoms and having 1 to 6, for example 3, unsaturations in the cis configuration for use in preventing or treating dyslipidemia in a subject. Dyslipidemia typically affects the biological membranes, including the biological membranes of non-adipocyte cells. It is generally linked to the excess presence in said biological membranes of saturated fatty acids, more particularly of saturated long-chain fatty acids, and/or of sterols. The amount of saturated fatty acids and/or of sterols is in particular deemed excessive, for example, when by deteriorating membrane plasticity it causes cellular dysfunction. In a preferred embodiment of the invention, said compound i) does not allow the production of diunsaturated phospholipids, in particular is not responsible for the introduction of diunsaturated phospholipids in the membrane of treated cells, typically does not restore, in the treated cell, a membrane phospholipid fatty acid composition comparable to that of the membrane phospholipids of a corresponding non-lipointoxicated cell, ii) is not a source of oleic acid for the treated cell, typically a source of oleic acid capable of restoring the membrane plasticity of the treated cell, and preferably iii) does not induce intracellular calcium mobilization and/or is not degraded by lipases.

Another object of the invention relates to a compound the polar head of which is of formula (I):

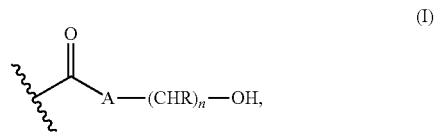

wherein:
A is a nitrogen or oxygen atom, preferably an oxygen atom,
n equals 2 or 3, preferably n equals 2, and
R is any chemical group,
for use in preventing or treating dyslipidemia in a subject, typically dyslipidemia as defined above.

Examples of preferred compounds according to invention i) not allowing the production of diunsaturated phospholipids, or not causing the introduction of such phospholipids in the membrane of treated cells, typically not restoring, in the treated cell, a membrane phospholipid fatty acid composition comparable to that of the membrane phospholipids of a corresponding non-lipointoxicated cell, and ii) not constituting a source of oleic acid for the treated cell, typically a source of oleic acid capable of restoring the membrane plasticity of the treated cell, are selected from mannide monooleate, 3-hydroxy-2,2-bis(hydroxymethyl)propyl oleate and N,N-diethanololeamide (unlike 1-oleoyl lysophosphatidic acid, or LPA, for example).

Examples of preferred compounds according to the invention not inducing intracellular calcium mobilization are mannide monooleate and 3-hydroxy-2,2-bis(hydroxymethyl)propyl oleate. Unlike OAG, a reference molecule for inducing cellular calcium mobilization (Marin & Cooper, 2006) or, alternatively, 1-oleoylglycerol and 2-oleoylglycerol (Iwasaki et al., 2008), these compounds are particularly advantageous in that they have a lower risk of toxicity by intracellular calcium-dependent deleterious processes, such as proliferation or apoptosis (Stutzmann G E et al., 2011).

An example of a preferred compound according to the invention that resists the degradative action of lipases is N,N-diethanololeamide.

The invention further relates to a compound as described in the present text for use in preventing or treating metabolic syndrome, typically at least one symptom or abnormality characteristic of metabolic syndrome, preferably at least two or three symptoms, said symptoms being selected from insulin resistance, insulin deficiency, hyperglycemia (typically fasting blood sugar≥about 5.5 mM), hypercholesterolemia, in particular hypercholesterolemia characterized by a low HDL cholesterol concentration (typically <about 1 mM for men and <about 1.3 mM for women), hypertriglyceridemia (typically TG≥about 1.7 mM), hypertension (typically blood pressure (BP)≥about 130/820 mm Hg), heart failure, and hepatic steatosis, preferably from insulin resistance, hyperglycemia (typically fasting blood sugar≥about 5.5 mM), hypercholesterolemia, in particular hypercholesterolemia characterized by a low HDL cholesterol concentration (typically <about 1 mM for men and <about 1.3 mM for women), hypertriglyceridemia (typically TG≥about 1.7 mM), hypertension (typically blood pressure (BP)≥about 130/820 mm Hg), heart failure, and hepatic steatosis. A particular object relates to a compound according to the invention for use in preventing or treating type 2 diabetes mellitus.

A particularly preferred compound according to the invention is mannide monooleate, which the inventors have shown, using mammalian pancreatic β-cells lipointoxicated by saturated fatty acids, is advantageously able to increase insulin secretion in subjects suffering from lipointoxication and/or type 2 diabetes mellitus by promoting in said subjects the maturation of proinsulin to insulin.

The invention further relates to a composition, in the form of a pharmaceutical composition, a functional food or a food supplement, comprising at least one compound according to the invention. A particular object typically relates to a pharmaceutical composition comprising, in addition to said at least one compound according to the invention, at least one other compound (different from the compounds according to the invention) that is therapeutically active (and recognized as such by persons skilled in the art).

The invention also relates to the use of such a composition for preventing or treating dyslipidemia in a subject, typically dyslipidemia in the biological membranes, including the biological membranes of non-adipocyte cells, in particular dyslipidemia linked to the excess presence in said biological membranes of fatty acids, more particularly of saturated long-chain and/or trans fatty acids, and/or of sterols. It also relates to the use of such a composition for preventing or treating metabolic syndrome in a subject, typically at least one symptom or abnormality characteristic of metabolic syndrome, preferably several symptoms (for example 2, 3, 4 or 5); preferably for preventing or treating type 2 diabetes mellitus. The uses described can also be advantageously implemented in combination with at least one other therapeutically active compound (recognized as therapeutically active by persons skilled in the art and different from the compounds according to the invention) in particular in the treatment of metabolic syndrome, typically of at least one symptom or abnormality characteristic of metabolic syndrome, and/or of type 2 diabetes mellitus.

DETAILED DESCRIPTION

The Inventors showed that SFA from an exogenous source (diet) or an endogenous source (hypoxia or alteration, by mutation, of the steps of fatty acid desaturation) accumulated in the phospholipids making up the cellular membranes, thus disrupting numerous processes, by altering the functionality of the intracellular organelles intervening in the protein secretory pathway (see FIG. 1).

To provide this demonstration, the Inventors developed a simple unicellular model (the hem1Δ strain elaborated from the baker's yeast *Saccharomyces cerevisiae*) reproducing all the effects of SFA and cholesterol observed in mammalian cells, in particular all the anomalies involved in the development of metabolic syndrome (Pineau et al., 2008 and Pineau et al., 2009).

In YPG medium (i.e., medium containing neither ergosterol (Erg) nor oleic acid (Ole)), the hem1Δ strain accumulates saturated fatty acids (in particular palmitic acid, C16:0) in its phospholipids, in particular in phosphatidylcholine (PC). It should be noted that ergosterol is the predominant sterol present in yeasts, and thus in yeasts it is the equivalent of cholesterol in humans.

The quadruple mutant (QM) strain (Petschnigg et al., 2009), in which the genes encoding the enzymes responsible for the synthesis of triglycerides and of sterol esters were deleted, is, in turn, incapable of transforming an exogenous supply of free fatty acids, of the oleic acid C18:1 type, to neutral lipids, so that this supply leads to deleterious stress due to the disruption of membrane plasticity equilibrium that it generates. The use of the QM strain in particular enabled the Inventors to carry out toxicity tests which clearly show the toxicity of oleic acid in such circumstances (see FIG. 4).

More precisely, the Inventors observed on the hem1Δ strains the negative effects on secretory vesicle formation of the accumulation of phospholipids bearing saturated chains (saturated PL) and of cholesterol in intracellular organelle membranes. This lipointoxication (endogenous because the cellular system of the hem1Δ strains only synthesizes SFA) disrupts the lipid environment of the endoplasmic reticulum (ER) membrane, alters the protein folding process (misfolding) and then triggers a complex response in said ER, a response known as the unfolded protein response (UPR). Saturation of this backup system leads to apoptotic cell death. In parallel, the Inventors were able to observe disruptions of Golgi apparatus vesiculation and an alteration of the trafficking of reference proteins (for example, Fur4p) between the Golgi apparatus and the plasma membrane. Concretely, the Inventors observed an alteration of the entire secretory pathway due to lipointoxication. In other words, the hem1Δ yeast strain enabled them to confirm both the effects of SFA on ER stress and the trafficking of proteins toward the plasma membrane.

The endoplasmic reticulum (ER) is involved in several fundamental cellular processes, including lipid synthesis, regulation of calcium homeostasis, and synthesis of proteins intended for the various organelles and the cell surface (for example, membrane proteins such as ion channels and transporters). The ER is also the site where membrane or secreted proteins are assembled and folded. Consequently, the UPR plays an essential role in maintaining ER integrity and functionality by enabling this organelle to manage the accumulation of misfolded proteins (Kincaid & Cooper, 2007; Zhang & Kaufman, 2006). It should be noted that SFA toxicity is associated, in pancreatic β-cells (responsible for insulin synthesis in mammals), with induction of the unfolded protein response (Cunha et al., 2008; Diakogiannaki & Morgan, 2008; Laybutt et al., 2007). Alkhateeb et al. (2007) and Kato et al. (2008) further observed that SFA accumulation alters the addressing of the insulin receptor and the glucose transporter Glut4 on the surface of muscle cells.

Schneider et al. (1999) observed that the membranes of the endoplasmic reticulum (ER) and of the Golgi apparatus consist of a large majority of unsaturated phospholipids (PL), whereas the level of saturated PL increases gradually in the most distal compartments in the secretory pathway to reach its maximum in the plasma membrane. High levels of unsaturated PL are expressed as high membrane fluidity, a crucial parameter for the recruitment of certain proteins essential to vesicle formation. A canonical example is provided by proteins of the Arf-GAP1 family, one being Gcs1p in yeast. It was shown that Gcs1p is a mediator of vesicular transport both between the Golgi apparatus and the ER and between the ER and the plasma membrane (Robinson et al., 2006). Interestingly, the deletion of the GCS1 gene causes a fragmentation of the Golgi apparatus and a disruption of post-Golgi vesicular traffic (Poon et al., 2001), as many phenomena as the Inventors themselves were able to observe in the hem1Δ yeast model, i.e., under SFA accumulation conditions (see Payet et al., 2013.).

Proteins of the Arf-GAP1 family respond to membrane curvature by being adsorbed on the membrane surface via a specific motif called ArfGAP1 lipid packing sensor (ALPS; Bigay et al., 2005). Concretely, the ALPS motif does not recognize membrane curvature as such, i.e., a curved geometry, but recognizes the loose packing of phospholipid polar heads (loose lipid packing), which is a consequence of membrane curvature (Bigay et al., 2005). The Inventors succeeded in showing that the high saturated PL levels under lipointoxication conditions are associated with an increase in membrane lipid packing (Deguil et al., 2011), and that this increase alters recruitment by the Golgi apparatus of Gcs1p from the cytoplasm (Payet et al., 2013). More generally, they showed that the accumulation of fatty acids, in particular of SFA, in the biological membranes caused the functional dysregulation of intracellular organelles including the Golgi apparatus and the endoplasmic reticulum (ER), and in particular a lower degree of vesiculation responsible for a decrease in the translocation of certain membrane transporters and receptors on the cell surface.

The cellular lipointoxications caused by the Inventors resulted, in vitro, from exposure to an exogenous source of fatty acids exclusively in saturated form ("exogenous" lipointoxication) or, alternatively, from an intrinsic incapacity of the cell to produce unsaturated forms of fatty acids ("endogenous" lipointoxication).

Using their hem1Δ yeast model, the Inventors showed that oleic acid (Ole), by being metabolized to phospholipids (PL) (see FIG. 1, loss of PL to SFA in favor of PL to UFA), restores the plasticity of membranes lipointoxicated beforehand by SFA. They also showed using the QM yeast strain that the beneficial effect observed was limited to the cells having the capacity to buffer excess exogenous UFA in the form of neutral lipids. In the cells not having this capacity, the surplus exogenous oleic acid leads ultimately to an abnormal proliferation of intracellular membranes which, by stressing the cells, will trigger their apoptosis.

The Inventors used their hem1Δ yeast model and the QM strain to screen molecules of interest likely to prevent or limit this phenomenon, ideally to counter the toxic effect of fatty acids that are present in excess and/or are poorly metabolized (i.e., esterified) and to correct all the disrupted phenomena. They thus discovered molecules able, in particular, to restore cellular functionality (by restoring membrane fluidity, for example) comparable to that encountered under non-pathological conditions.

The effectiveness of the molecules preselected by the Inventors, i.e., their ability to restore cellular functionality comparable to that encountered in non-pathological conditions, even in the case of established dyslipidemias, was then tested and shown by these same Inventors in mammalian pancreatic β-cells, in particular in rat pancreatic β-cells (BRIN-BD11 cell line). Furthermore, the Inventors were able to demonstrate that the compounds of interest have a very limited influence on cellular phenomena such as the calcium mobilization responsible for inducing cell proliferation and apoptosis. They are thus less toxic than the compounds, such as OAG, that induce or promote, on the contrary, such cellular calcium mobilization. Similarly, certain compounds were shown particularly effective in restoring the conversion of proinsulin to insulin in mammalian pancreatic β-cells, in particular in mouse pancreatic β-cells (MIN6 cell line).

The invention thus relates to a compound comprising a polar head, comprising at least one hydroxyl residue, on which is grafted a single unsaturated fatty acid comprising between 16 and 24, for example between 16 and 20, typically 18, carbon atoms and having 1 to 6, for example 3, unsaturations in the cis configuration (identified in the present text as "compound of interest") for use in preventing or treating dyslipidemia in a subject.

The subject concerned is an animal, typically a mammal, for example a mammal selected from a mouse, a rat, a pig and a human being. The subject concerned is preferably a human being.

In the context of the present description, the dyslipidemia the prevention or treatment of which is sought typically affects the biological membranes, in particular the biological membranes of non-adipocyte cells. It is generally linked to the excess presence in said biological membranes of fatty acids, more particularly of saturated long-chain and/or trans fatty acids, and/or of sterols. Dyslipidemia is typically responsible for the intoxication (lipointoxication) of the non-adipocyte cells at the origin of the dysfunction or the apoptosis of said cells by decreasing, even suppressing, the fluidity of the plasma membrane thereof and/or the organelle membranes thereof.

In a particular embodiment of the invention, dyslipidemia is associated with the presence in the subject of metabolic syndrome, typically of at least one symptom of metabolic syndrome, preferably of at least two or three symptoms, said symptoms being selected from insulin resistance, insulin deficiency, hyperglycemia (typically fasting blood sugar≥about 5.5 mM), hypercholesterolemia, in particular hypercholesterolemia characterized by a low HDL cholesterol concentration (typically <about 1 mM for men and <about 1.3 mM for women), hypertriglyceridemia (typically TG≥about 1.7 mM), hypertension (typically blood pressure (BP)≥about 130/820 mm Hg), heart failure, and hepatic steatosis, preferably from insulin resistance, hyperglycemia (typically fasting blood sugar≥about 5.5 mM), hypercholesterolemia, in particular hypercholesterolemia characterized by a low HDL cholesterol concentration (typically <about 1 mM for men and <about 1.3 mM for women), hypertriglyceridemia (typically TG≥about 1.7 mM), hypertension (typically blood pressure (BP)≥about 130/820 mm Hg), heart failure, and hepatic steatosis.

As can be seen from the present description, the expression "excess presence" of fatty acids, in particular of SFA, and/or of sterols, is synonymous with "lipointoxication," for example exogenous lipointoxication or, alternatively, endogenous lipointoxication (hypoxic, for example), and refers to the presence, in a non-adipocyte cell, in particular of saturated and/or trans fatty acids, and/or of sterols in an amount sufficient to disrupt the secretory pathway described above and thus to alter cellular functioning (typically the protein secretory pathway and, consequently, the function of said proteins), or, on a higher level, to alter as a consequence the functioning of the corresponding organ.

Renal lipointoxication appears, for example, when saturated fatty acids, in particular saturated long-chain fatty acids, are stored in the cells of the kidney and of the proximal convoluted tubule. Such storage leads to tubulointerstitial inflammation and to fibrosis, even to kidney failure, and to the death of the subject concerned in the most severe cases. Still by way of example, lipointoxication of the pancreas is typically diagnosed by the storing of saturated fatty acids, in particular of saturated long-chain fatty acids, in membrane phospholipids in pancreatic β-cells.

On a cellular scale, lipointoxication is typically diagnosed by the detection of a change in the fatty acid content of the phospholipids (PL) of the biological membranes (the phospholipid species of phosphatidylcholine (PC) in particular) and, in particular, by the depletion of the PL forms to UFA to the benefit of PL to SFA. In the image of the procedure described in the Examples section of the present description, such a lipidomic signature can be shown following the extraction of total cellular lipids, the purification of their phospholipids and the mass spectrometry analysis of the latter (Deguil et al., 2011).

Furthermore, this cellular lipointoxication can appear by the induction of the unfolded protein response (UPR). As shown in the Examples section, it is possible, in vitro, to detect and measure this UPR by analyzing the expression of a reporter gene (such as the lacZ gene encoding 0-galactosidase, whose enzyme activity can be quantified) containing in its promoter sequence one or more, for example four, UPR elements (UPRE) specific to a gene characteristically induced during the triggering of said response, for example a gene selected from CHOP, BiP, GRP78 and ATF4 (Laybutt et al., 2007). Alternatively, the triggering of the UPR in response to lipointoxication can be detected and measured by quantifying the proportion of the active forms of certain key proteins in this cellular event cascade. That is the case of the protein eIF2α, the abundance of which in phosphorylated active form is proportional to UPR activation state. As explained in the Examples section, the amount of the phosphorylated active form can be evaluated by densitometry of images obtained after Western blot (Dhayal & Morgan, 2011).

In the context of the present invention, the UPR can be advantageously detected or measured by detecting or measuring the expression of a gene or the activity of a protein involved in the UPR, as explained above.

A compound of particular interest is a compound as defined above the polar head of which is of formula (I):

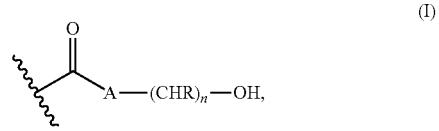

wherein:

A is typically an oxygen atom or an $NR_1$ group, with $R_1$=H or a $C_1$-$C_6$ alkyl optionally substituted with OH, and A is preferably an oxygen atom or NH or $NCH_3$ or $NCH_2CH_2OH$, and more preferably A is an oxygen atom, n=2 or 3, preferably n=2, and R is any chemical group and can be different from one (CHR) group to another.

In formula (I), the bond broken by zigzags represents the bond between the polar head and the carbon chain of the unsaturated fatty acid, the C=O group of formula (I) being the C=O of the unsaturated fatty acid.

Preferably, R is a group comprising only carbon, hydrogen and oxygen atoms.

Preferably, R is a saturated group comprising only carbon, hydrogen and oxygen atoms.

Preferably, the $(CHR)_n$—OH radical is a derivative of glycerol, of erythritol or of a monosaccharide such as mannose.

In the present invention, each hydroxyl residue can be phosphated independently.

Examples of compounds of interest usable in the context of the invention for preventing or treating dyslipidemia are identified below:

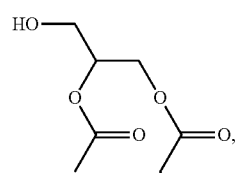
1-oleoyl-2-acetyl-sn-glycerol (OAG)
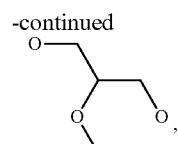
2-arachidonoylglycerol (2-AG),
-continued
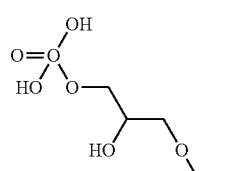
1-oleoyl-sn-glycerol-3-phosphate (1-oleoyl lysophosphatidic acid, or LPA)
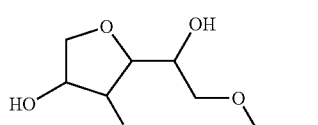
mannide monooleate

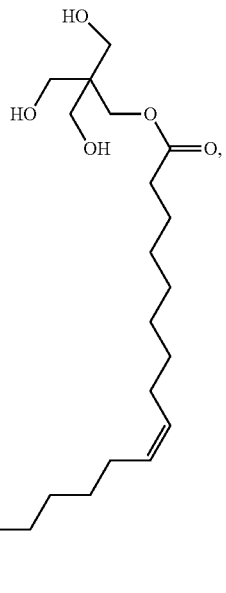
3-hydroxy-2,2-bis(hydroxymethyl)propyl oleate
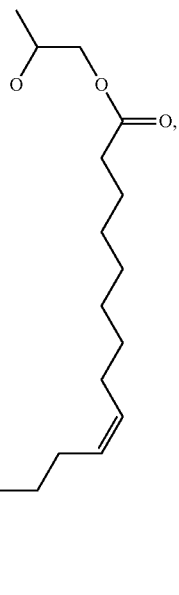
propylene glycol monooleate,
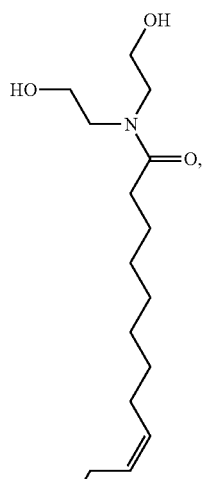
N,N-diethanololeamide
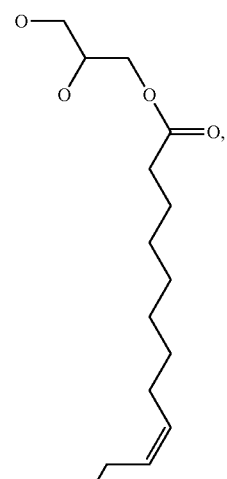
1-oleoyl glycerol -continued

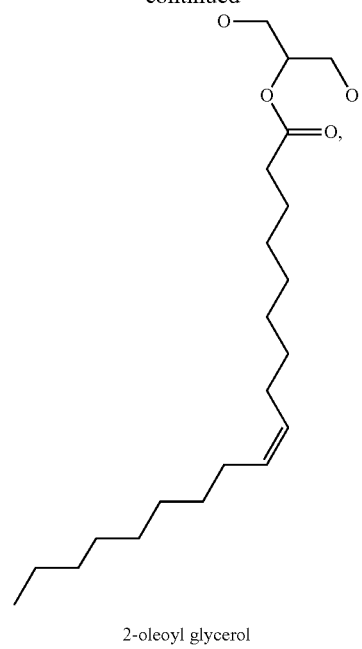

2-oleoyl glycerol

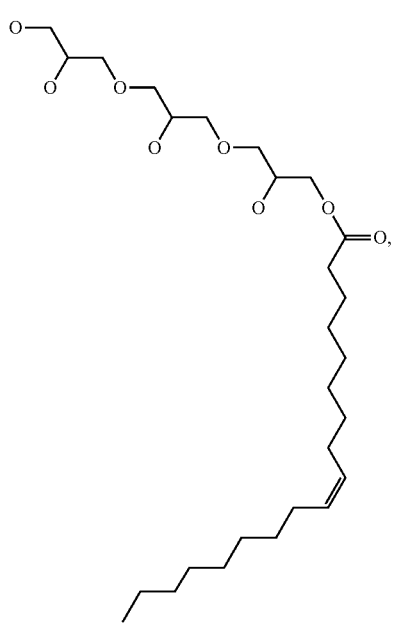

oleic acid monoester with triglycerol

-continued

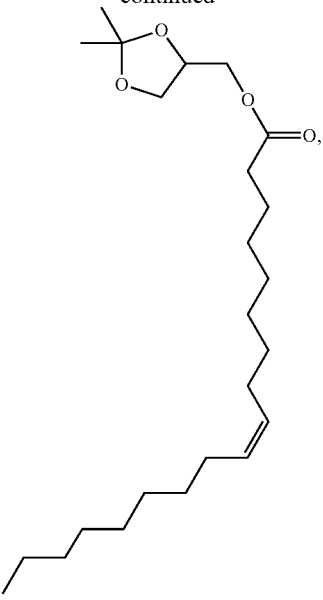

(Z)-9-octadecenoic acid-(2,2-dimethyl-1,3-dioxolan-4-yl)methyl ester

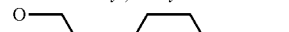
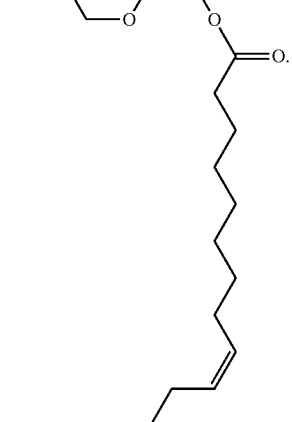

diethylene glycol monooleate

Compounds of interest usable in the context of the invention for preventing or treating dyslipidemia are selected for example from 1-oleoyl-2-acetyl-sn-glycerol (OAG), 1-oleoyl-sn-glycerol-3-phosphate (1-oleoyl lysophosphatidic acid, or LPA), 2-arachidonoylglycerol (2-AG), mannide monooleate, 3-hydroxy-2,2-bis(hydroxymethyl)propyl oleate, N,N-diethanololeamide, propylene glycol monooleate, oleic acid monoester with triglycerol, and (Z)-9-octadecenoic acid-(2,2-dimethyl-1,3-dioxolan-4-yl) methyl ester.

Preferably, the compounds usable in the context of the invention for preventing or treating dyslipidemia, in particular lipointoxication associated with a metabolic disease such as type 2 diabetes mellitus and/or hypoxic lipointoxication, are selected from mannide monooleate, 3-hydroxy-2,2-bis (hydroxymethyl)propyl oleate and N,N-diethanololeamide.

A particularly preferred compound of interest for preventing or treating dyslipidemia, in particular in the context of the prevention and/or treatment of a metabolic disease, and/or a symptom or abnormality characteristic of metabolic syndrome, preferably type 2 diabetes mellitus, is mannide monooleate.

The compounds of interest are used in the context of the invention for preventing or treating dyslipidemias, typically by restoring biological membrane fluidity. An advantageous feature of these compounds is that, unlike the unsaturated fatty acids used in the prior art, they are nontoxic to cells unable to synthesize neutral lipids, typically triglycerides and/or esterified sterols. These compounds are in particular nontoxic to pancreatic cells (pancreatic β-cells and pancreatic α-cells). They are also preferably nontoxic to renal, hepatic, cardiac and muscle cells. They are in addition preferably advantageously capable of restoring the functionality of a lipointoxicated cell and, if need be, that of the related organ.

A typical compound of interest of the invention advantageously has the following properties:
  (i) it restores the growth of a lipointoxicated hem1Δ mutant of the yeast *Saccharomyces cerevisiae*,
  (ii) it reduces or suppresses the unfolded protein response (UPR),
  (iii) it is not toxic to a quadruple mutant (QM) of the yeast *Saccharomyces cerevisiae*, and/or
  (iv) it reduces or suppresses the apoptotic death of a lipointoxicated mammalian cell.

Particular compounds used in the context of the invention are capable of restoring the growth of a lipointoxicated hem1Δ mutant of the yeast *Saccharomyces cerevisiae* and/or reducing or suppressing the unfolded protein response (UPR), typically the UPR induced by lipointoxication (whether the latter is endogenous or exogenous in nature).

Particular compounds used in the context of the invention are nontoxic to the QM strain yeasts.

Particular compounds used in the context of the invention are able to reduce or suppress the apoptotic death of lipointoxicated mammalian cells.

Among the compounds described usable in the context of the invention, some act directly on lipid content, i.e., on the fatty acid composition of phospholipids present in the cellular membranes. Examples of such compounds are 1-oleoyl-sn-glycerol-3-phosphate (1-oleoyl lysophosphatidic acid, or LPA) and propylene glycol monooleate.

Others compounds usable in the context of the invention restore membrane fluidity, and thus membrane functionality, without restoring a normal diunsaturated phospholipid composition in the cell membranes. A preferred example of such a compound is 1-oleoyl-2-acetyl-sn-glycerol (OAG). More preferred examples are mannide monooleate, 3-hydroxy-2,2-bis(hydroxymethyl)propyl oleate and N,N-diethanololeamide.

In a preferred embodiment of the invention, the compounds of interest are used for preventing and/or treating a pathological condition selected from metabolic syndrome and/or a symptom or abnormality characteristic of metabolic syndrome, preferably for preventing or treating type 2 diabetes mellitus.

In a particular embodiment of the invention, the compounds of interest are used for preventing and/or treating metabolic syndrome, typically at least one symptom of metabolic syndrome, preferably at least two or three symptoms, said symptoms being selected from insulin resistance, insulin deficiency, hyperglycemia (typically fasting blood sugar≥about 5.5 mM), hypercholesterolemia, in particular hypercholesterolemia characterized by a low HDL cholesterol concentration (typically <about 1 mM for men and <about 1.3 mM for women), hypertriglyceridemia (typically TG≥about 1.7 mM), hypertension (typically blood pressure (BP)≥about 130/820 mm Hg), heart failure, and hepatic steatosis, preferably from insulin resistance, hyperglycemia (typically fasting blood sugar≥about 5.5 mM), hypercholesterolemia, in particular hypercholesterolemia characterized by a low HDL cholesterol concentration (typically <about 1 mM for men and <about 1.3 mM for women), hypertriglyceridemia (typically TG≥about 1.7 mM), hypertension (typically blood pressure (BP)≥about 130/820 mm Hg), heart failure, and hepatic steatosis.

As explained above, for type 2 diabetes mellitus, the current therapeutic approaches target parameters intervening downstream from the initial dyslipidemias. Although validated in physiological contexts in the laboratory, these treatments suffer from a lack of effectiveness due to the global disruption of the membrane mechanisms noted in cases of established lipointoxication, appearing in particular as altered or ineffective membrane fluidity (in that the cell concerned is no longer functional). There is in particular today no molecule or compound for treating dyslipidemias affecting cells unable to synthesize neutral lipids, in particular non-adipocyte cells.

In a preferred embodiment of the invention, at least one compound of interest as described in the present text is used for preventing and/or treating type 2 diabetes mellitus. Mannide monooleate is an example of a compound of interest used preferably for preventing and/or treating type 2 diabetes mellitus.

This at least one compound of interest can be used, in a particular embodiment of the invention, in combination with a distinct compound known to the skilled person and traditionally used in the prevention or treatment of type 2 diabetes mellitus, said distinct compound preferably being selected from biguanide, glitazone, sulfonamide-based hypoglycemic, glinide, DPP-4 inhibitor, incretin mimetic and α-glucosidase inhibitor.

Another object of the invention further relates to a composition in the form of a pharmaceutical composition, a functional food, a food supplement or complement, comprising at least one compound of interest according to the invention (identified in the present text as a "composition of interest").

A particular object typically relates to a pharmaceutical composition comprising in addition to said at least one compound of interest according to the invention, at least one other compound (different from the compounds of interest used in the context of the invention for preventing or treating dyslipidemia without inducing toxicity in non-adipocyte cells) that is therapeutically active (and recognized as such by persons skilled in the art), in particular a compound active in the prevention or treatment of a symptom or abnormality characteristic of metabolic syndrome, and/or type 2 diabetes mellitus (as described in the present text, for example).

The invention also relates to a composition as described in the present text for use in preventing or treating dyslipidemia, typically a pathological condition selected from metabolic syndrome and/or a symptom or abnormality characteristic of metabolic syndrome, preferably in preventing or treating type 2 diabetes mellitus.

The term "treatment" refers to curative, symptomatic or preventive treatment. The compounds of the present invention can thus be used in subjects (such as mammals, in particular humans) suffering from a declared disease. The compounds of the present invention can also be used to delay or slow the progression or to prevent further progression of the disease, thus improving the condition of the subjects. Finally, the compounds of the present invention can be administered "preventively" to subjects who are not ill but who could develop the disease normally or who are at high risk of developing the disease.

The compounds of interest or compositions according to the invention can be administered in various ways and in various forms.

Thus, in a typical embodiment, the compound(s) of interest are administered to the subject, together or separately, and the compound(s) of interest or composition(s) according to the invention are administered continuously or sequentially, one or more times per day (daily administration), one or more times per week (weekly administration), or one or more times per month (monthly administration), throughout the duration of the treatment, i.e., until the symptomatic improvement of the treated pathology, preferably the disappearance of all or part of said symptoms.

If necessary, the daily dose can, for example, be administered in two, three, four, five, six or more doses per day or in multiple sub-doses administered over suitable intervals during the day.

Said compounds or compositions can, for example, be administered systemically, orally, parenterally, by inhalation or by injection, such as intravenously, intraperitoneally, intramuscularly, subcutaneously, transdermally, intraarterially, etc. Being a long-term treatment, the preferred route of administration will be sublingual, oral, intraperitoneal or transcutaneous.

The compositions can be formulated as injectable suspensions, oils, suppositories, hard-shelled capsules, soft-shelled capsules, aerosols, etc., optionally by means of galenic forms or devices providing extended and/or delayed release. For injections, the compounds are generally packaged as liquid suspensions, which can be injected by means of syringes or perfusions, for example.

It is understood that the flow rate and/or the injected dose can be adapted by the skilled person according to the patient, the pathology, the mode of administration, etc. Generally, the daily dose of the compound will be the minimum amount needed to obtain a therapeutic effect.

The amount of the compound present in the therapeutic composition can be adjusted so as to obtain a circulating level of active ingredient needed to obtain the desired therapeutic effect for a particular patient, a composition, a mode of administration, and preferably without toxicity to the patient. The amount selected will depend on multiple factors, in particular the route of administration, the duration of administration, the hour of administration, the rate of elimination of the compound, the various products used in combination with the compound, the patient's age, weight, physical condition and medical history, and any other information known in medicine.

Typically, the compounds are administered in doses varying between 1 µg and 2 g per administration, preferably 0.1 mg to 1 g per administration. In addition, the compositions according to the invention can further comprise other agents or active ingredients as explained above. The compositions according to the invention can also comprise one or more pharmaceutically acceptable excipients or carriers. Mention may be made, for example, of saline, physiological, isotonic and buffer solutions, etc., compatible with pharmaceutical use and known to the skilled person. The compositions can contain one or more agents or carriers selected from dispersants, solubilizers, stabilizers, preservatives, etc.

The invention also relates to methods for preventing or treating dyslipidemia in a subject comprising the administration to a subject suffering from dyslipidemia or likely to develop dyslipidemia of a compound or a composition of interest as described in the present text for preventing or treating said dyslipidemia.

It further relates to methods for preventing in a subject, or for treating in an ill subject, a pathological condition selected from metabolic syndrome, a symptom or abnormality characteristic of metabolic syndrome, and type 2 diabetes mellitus. These methods all comprise a step of administering to a subject suffering from such a pathological condition or likely to develop such a pathological condition a compound or a composition of interest as described in the present text for preventing or treating said pathology.

The following figures and examples illustrate the invention without limiting its scope.

FIGURE LEGENDS

FIG. 1: Secretory pathway and membrane plasticity

Following their synthesis, membrane or secreted proteins (the cell's molecular "tools") must undergo maturation steps inside the cell. Each step of this process, called the "secretory pathway", takes place in a specific subcellular compartment (the endoplasmic reticulum (ER) and Golgi apparatus in particular). In order to obtain mature proteins, functional intracellular transport between the various endomembrane systems is thus required. This flux is influenced by, among other things, intracellular compartment membrane plasticity, which is itself directly correlated with the nature of the phospholipids (PL) making up the membranes. In particular, it is acknowledged that the presence of saturated fatty acids (SFA) in PL decreases membrane fluidity whereas PL bearing unsaturated fatty acids (UFA) form more fluid membranes.

The beneficial effect of oleic acid (Ole) is observed in the cells having the capacity to buffer excess exogenous UFA in the form of neutral lipids (triglycerides (TG) or esterified sterols (ES) stored in the form of lipid droplets (LD)). In the cells not having this capacity, the surplus exogenous oleate leads ultimately to a proliferation of the intracellular membranes which, by causing cellular stress, will trigger apoptosis.

Figure 2:
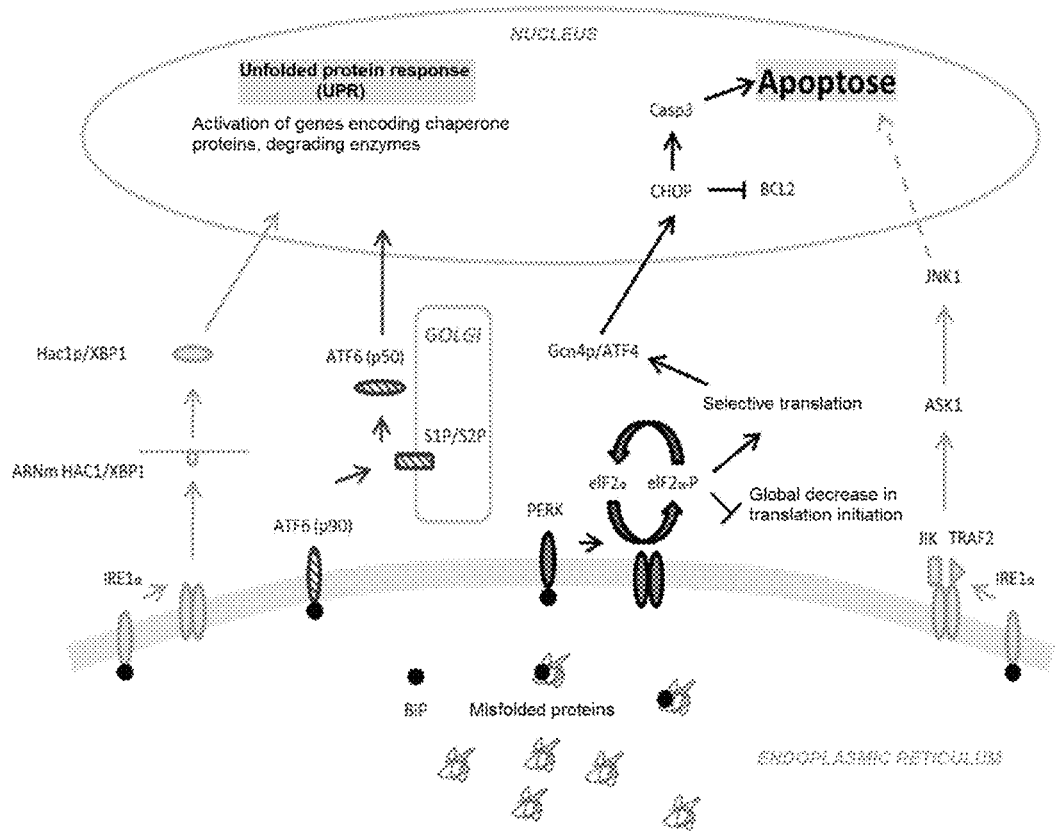

FIG. 2: UPR pathways in higher eukaryotes (Pineau & Ferreira, 2010).

Figure 3:
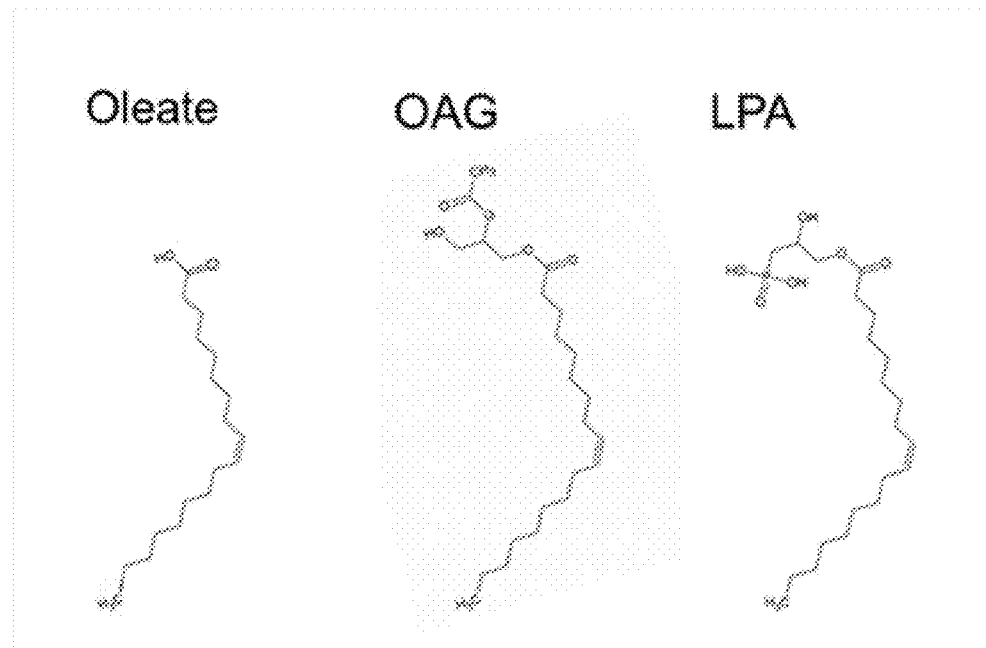
Figure 3:
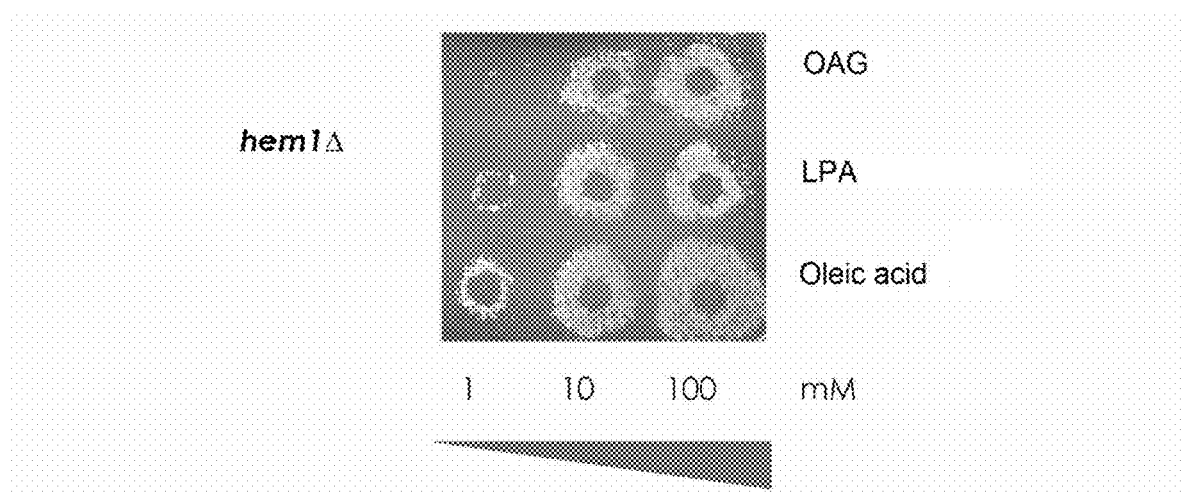

FIG. 3: Oleic acid, OAG and LPA restore the growth of lipointoxicated yeast.

A) Molecular structures of oleic acid, OAG and LPA. B) Restoration of the growth (after 3 days) of hem1Δ yeasts grown under SFA accumulation conditions, in the presence of increasing concentrations of oleic acid, OAG and LPA.

Figure 4:
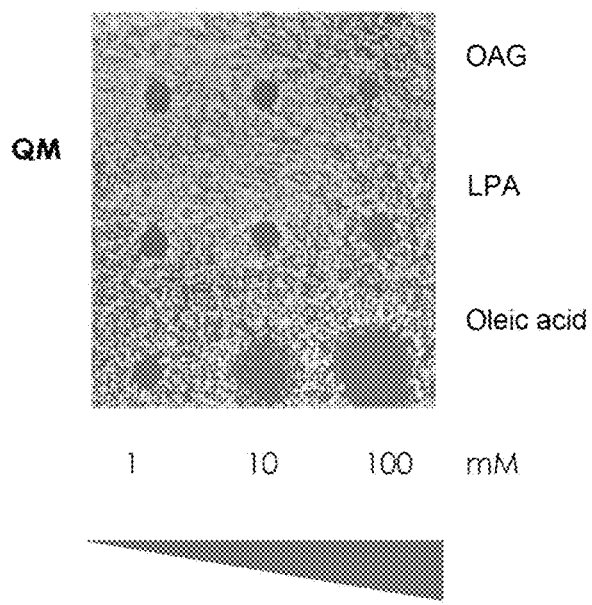

FIG. 4: OAG and LPA are not toxic to cells not synthesizing triglycerides.

Drops (5 µl) of OAG, LPA or oleic acid were deposited, from stock solutions at the indicated concentrations, on the surface of an agar medium over which the QM strain had been spread beforehand. After three days, growth inhibition halos (absence of colonies) can be observed in the case of oleic acid. These halos are, however, not observed in the presence of LPA or of OAG.

Figure 5:
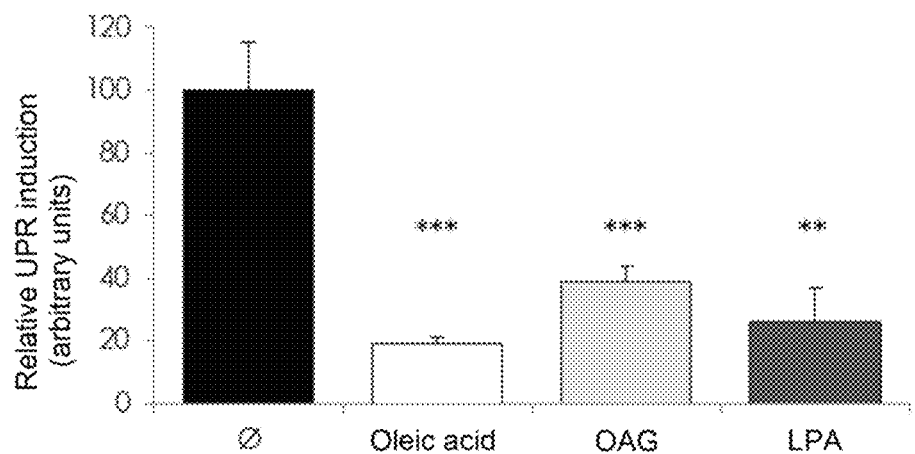

FIG. 5: OAG and LPA reduce the unfolded protein response (UPR) in lipointoxicated yeasts.

A plasmid construction bearing a fusion gene, corresponding to the coding sequence of the lacZ gene placed under the control of an artificial promoter containing four UPR elements (UPRE), was introduced into a hem1Δ yeast strain, as described by Pineau et al. (2009). During UPR induction, the transcription factor Hac1p/XBP1p is activated and binds to the fusion gene UPRE, leading to the transcription of the lacZ gene. As lacZ encodes β-galactosidase, the level of UPR induction is thus measured by detecting the corresponding enzyme activity. The hem1Δ yeast strain was grown in liquid medium inducing SFA accumulation with no other addition (0), or in the same medium supplemented with 200 µM oleic acid, OAG or LPA, as indicated.

Figure 6:
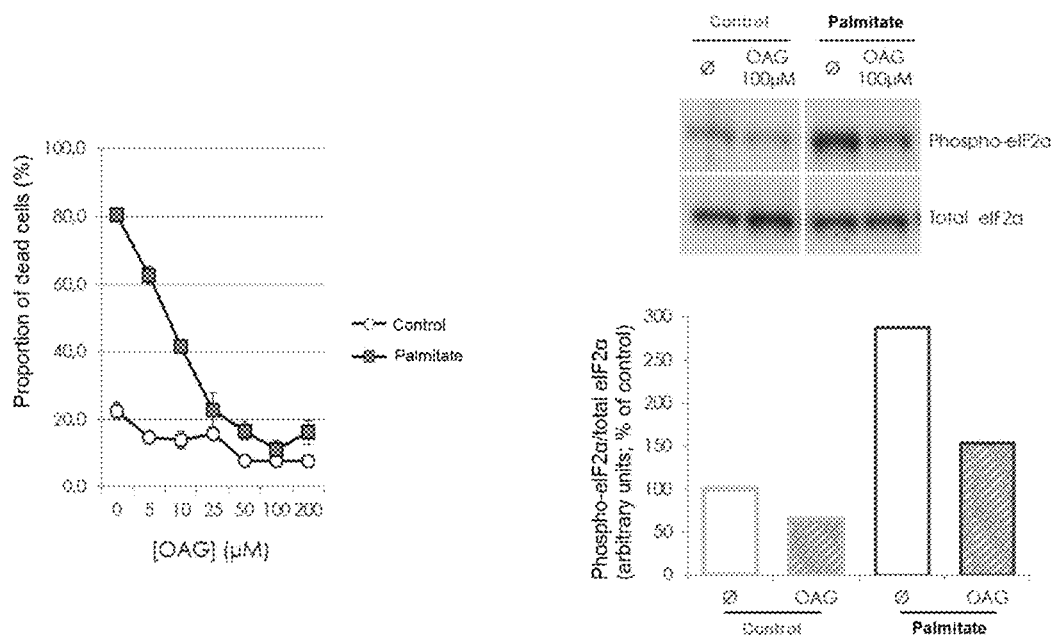

FIG. 6: OAG prevents apoptosis of pancreatic β-cells in the presence of saturated fatty acids by reducing UPR induction level.

Pancreatic β-cells, BRIN-BD11, were grown under control conditions or in the presence of an exogenous source of saturated fatty acid (200 µM palmitic acid), as described by Dhayal & Morgan (2011), in order to generate lipointoxication conditions, with or without the addition of OAG. A) The proportion of dead cells was estimated in the absence (control) or presence of palmitic acid, for increasing concentrations of OAG. B) eIF2α phosphorylation levels were also analyzed under the various conditions by Western blot, in the presence or absence (Ø) of OAG, and were normalized to total eIF2α. As phosphorylation level is correlated with UPR intensity, this experiment shows that OAG reduces the UPR induced by palmitic acid accumulation.

Figure 7:
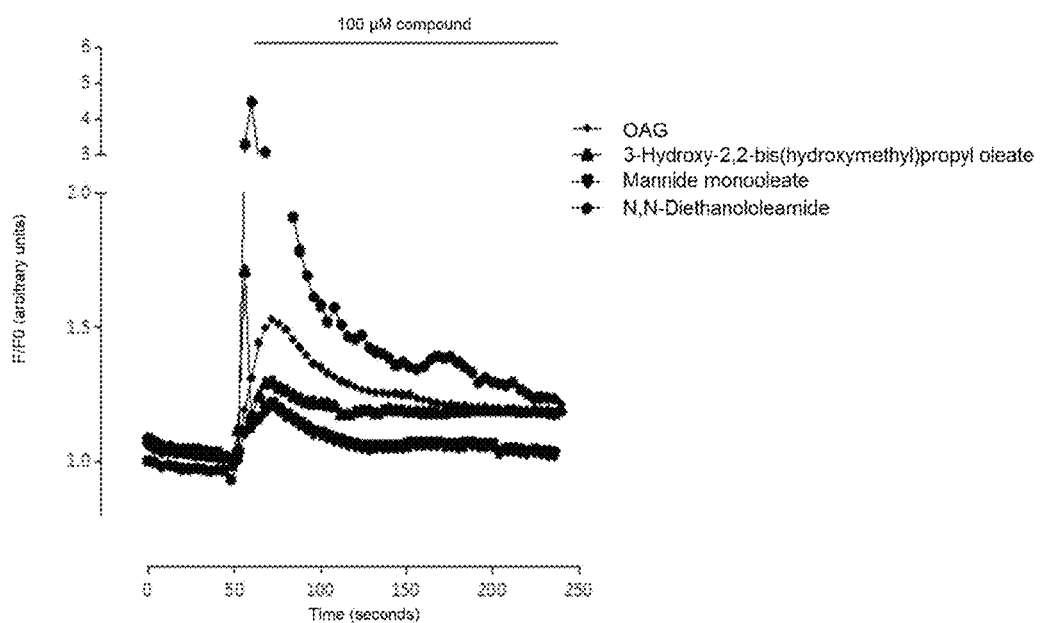

FIG. 7: 3-Hydroxy-2,2-bis(hydroxymethyl)propyl oleate and mannide monooleate do not induce calcium mobilization.

Human epithelial cells, CFBE, were loaded with a fluorescent calcium probe and then exposed to 100 µM OAG, 3-hydroxy-2,2-bis(hydroxymethyl)propyl oleate, mannide monooleate or N,N-diethanololeamide. The changes in fluorescence intensity, associated with intracellular calcium movements, were then recorded (see Vachel et al., 2013). The results obtained indicate that 3-hydroxy-2,2-bis(hydroxymethyl)propyl oleate and mannide monooleate have a very weak influence on the depletion of cellular calcium stores (i.e., they do not induce cellular calcium mobilization) in comparison with OAG, and that these compounds thus have very limited risks of cellular toxicity.

Figure 8:
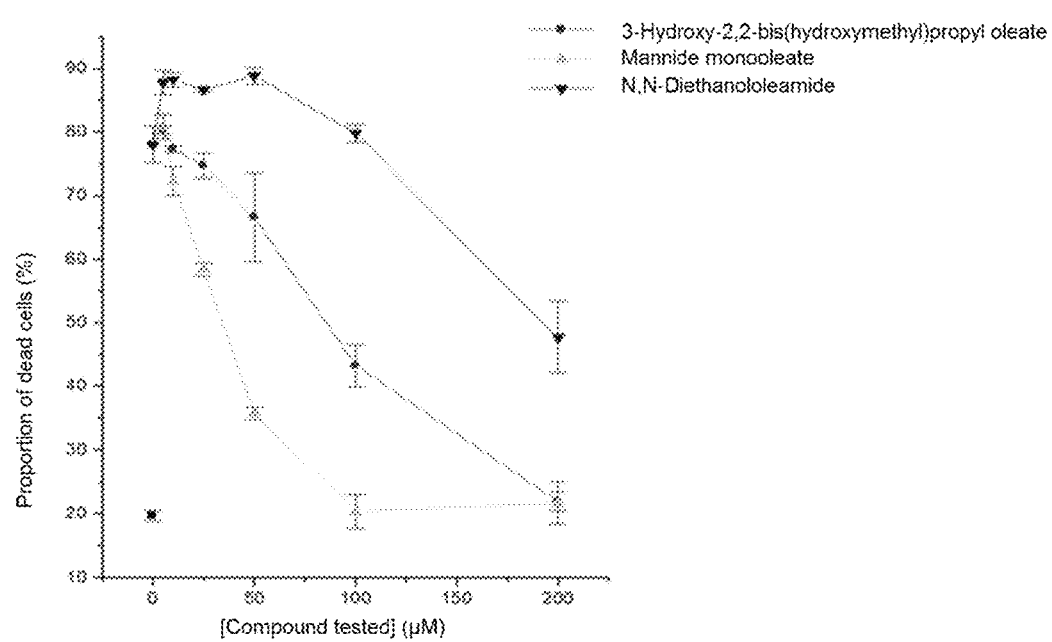

FIG. 8: 3-Hydroxy-2,2-bis(hydroxymethyl)propyl oleate, mannide monooleate and N,N-diethanololeamide prevent apoptosis of pancreatic β-cells in the presence of saturated fatty acids.

Pancreatic β-cells, BRIN-BD11, were grown in the presence of an exogenous source of saturated fatty acid (200 µM palmitic acid), as described by Dhayal & Morgan (2011), in order to generate lipointoxication conditions, before the addition of 3-hydroxy-2,2-bis(hydroxymethyl)propyl oleate, mannide monooleate or N,N-diethanololeamide. Together with the data of FIG. 6, these results indicate that the three compounds of interest prevent the death of lipointoxication-induced pancreatic β-cells.

Figure 9:
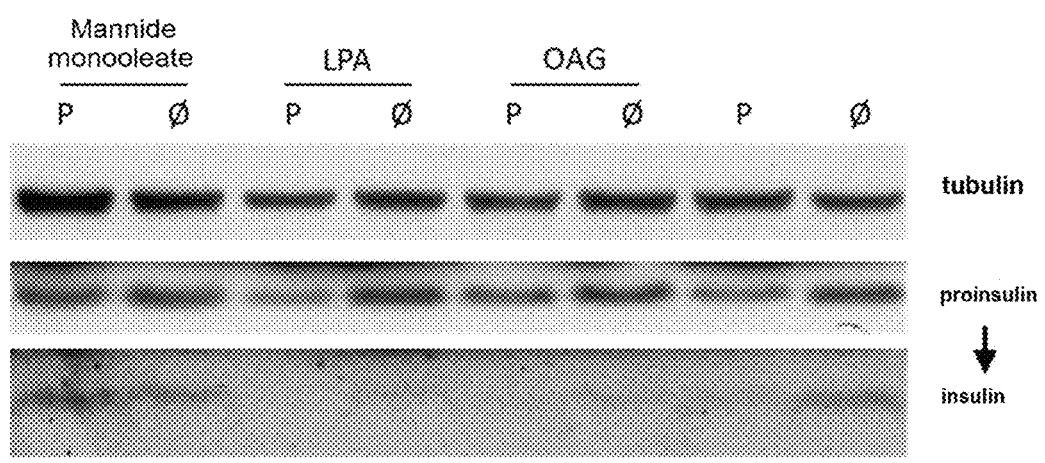

FIG. 9: Mannide monooleate restores proinsulin maturation under lipointoxication conditions in mammalian pancreatic β-cells.

Pancreatic β-cells, MIN6, were grown under control conditions (0) or, alternatively, in the presence of an exogenous source of 400 µM palmitic acid (P), for 48 hours, as described by Boslem et al. (2011), in order to generate lipointoxication conditions. During the final 24 hours of growth, 200 µM OAG, LPA or mannide monooleate was added or not as mentioned. Under these conditions, the protein samples were subjected to Western blot and the results obtained indicate that only mannide monooleate restores the maturation of proinsulin to insulin under lipointoxication conditions.

Figure 10:
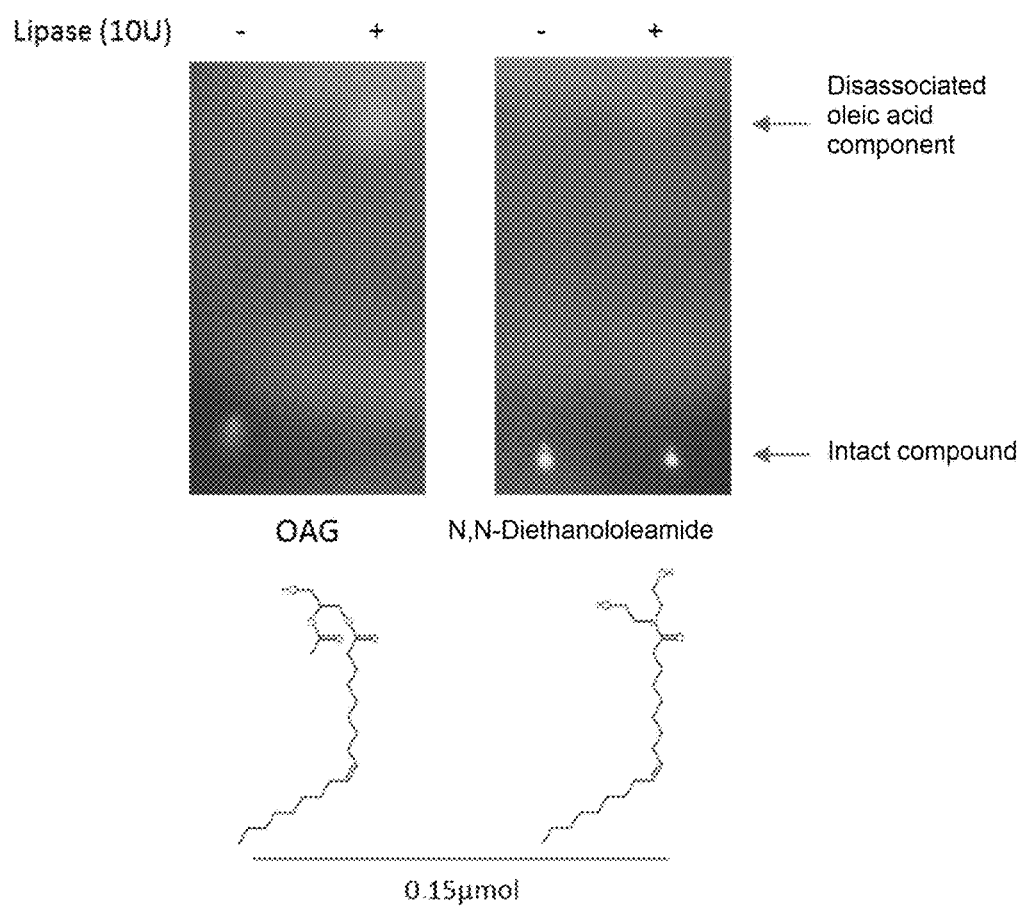

FIG. 10: N,N-Diethanololeamide resists the hydrolytic activity of lipases.

OAG (15 µmol) and N,N-diethanololeamide were subjected (+) or not (−) to exposure to 10 U of lipase for 30 minutes at 37° C. Following the incubation, the lipid species were extracted from the samples before being separated by thin-layer chromatography. The molecular species of interest are annotated and the results indicate that, unlike OAG, N,N-diethanololeamide resists hydrolysis by lipases.

EXAMPLES

A/ Yeast Strains and Mammalian Cell Lines

The *Saccharomyces cerevisiae* yeast strains listed in Table 1 are used for the various tests of growth restoration, to demonstrate toxicities, for the analysis of the fatty acid content of cellular phospholipids, and for the tests of unfolded protein response (UPR) triggering.

UPR activation state and lipointoxication-induced cell death were also analyzed in rat pancreatic β-cell line BRIN-BD 11.

Furthermore, the tests of calcium mobilization were carried out on human epithelial cells, CFBE, and the insulin maturation experiments were carried out on a mouse pancreatic β-cell line, MIN6.

TABLE 1

Yeast strains used

| Strain | Genotype | Origin |
|---|---|---|
| hem1Δ | MATa trp1 his3 ura3 leu2 hem1::LEU2 | FY1679α × FYHO4 |
| QM (H1246 W303) | MATα are1::HIS3 are2::LEU2 dga1::KanMX4 lro1::TRP1 ADE2 met ura3 | ScanBi Ltd., Alnarp, Sweden |
| WT (G175 W303) | MATa ADE2 MET his3 leu2 ura3 trp1 | ScanBi Ltd., Alnarp, Sweden |

B/ Lipointoxication of hem1Δ Yeasts

The strain bearing the hem1Δ mutation is grown, under aerobic conditions, with shaking and at 28° C., in liquid YPG$^-$ medium (YPG (1% yeast extract (w/v), 1% peptone (w/v) and 2% glucose (w/v)) supplemented with 80 µg/ml 6-aminolevulinic acid (ALA)). Lipointoxication by saturated fatty acids (SFA) is caused by depletion of unsaturated fatty acids (UFA), the synthesis of which is dependent on the presence of heme (the prosthetic group of the Ole1p enzyme in particular), by transfer to YPG$^+$ medium (YPG supplemented with 80 µg/ml ergosterol to compensate for the sterol depletion obtained under this condition). Lipointoxication can be induced on solid YPG$^+$ medium+2% agar (w/v) by transferring 3500 cells (hem1Δ from preculture in YPG$^-$) per cm$^2$ or, alternatively, in liquid medium by inoculating 2×10$^6$ cells/ml YPG$^+$. Classically, the effects of SFA lipointoxication are analyzed 7 hours after the transfer to YPG$^+$ medium. The ability of a compound to counter the deleterious effects of SFA lipointoxication, in turn, is evaluated successively to the addition of this compound on (or in) the YPG$^+$ transfer medium, after seeding with the cells.

C/ Lipointoxication of Rat Pancreatic β-Cells by Palmitic Acid

1) Preparation of Lipid Reagents:

The lipid species are prepared in ethanol before being complexed with bovine serum albumin (BSA, first depleted of fatty acids) by incubation for 1 hour at 37° C. The palmitic acid stock solution is obtained by adding one volume of ethanol before the whole is heated to 70° C. for homogenization. OAG and LPA solutions are prepared in 100% ethanol at room temperature. For the incubations of mammalian cells, the final BSA and ethanol concentrations in the culture medium are kept at 1% and 0.5% (w/v), respectively.

2) Tests of Cell Viability:

The rat pancreatic β-cell line (BRIN-BD11) is grown in complete RPMI-1640 medium, containing 11 mM glucose and supplemented with 10% (v/v) fetal calf serum (FCS), 2 mM L-glutamine, 100 U/ml penicillin and 100 µg/ml streptomycin. For each experiment, the cells are first seeded at a density of $0.5 \times 10^5$ cells/ml in 6-well plates for 24 hours. Thereafter, the complete medium is replaced by an equivalent lacking FCS but containing the lipid reagents of interest, at the desired concentrations, complexed with BSA. Under the control conditions, identical amounts of BSA and ethanol are then used. At the conclusion of the incubations, all of the cells (dead and living) are collected and centrifuged at 300 g for 5 minutes. The cell pellet is then resuspended in 200 µl of medium and then the DNA of the dead cells (having lost their plasma membrane integrity) is stained with propidium iodide (PI) by adding 200 µl of a 20 µg/ml solution of PI in FACS buffer (phosphate-buffered saline (PBS), 2% (v/v) FCS, 10 mM sodium azide). After incubation on ice for 10 minutes, the samples thus obtained are analyzed by flow cytometry. A Beckman Coulter EPICS XL MCL is used for the quantification, an FL3 channel is used to detect the emissions of the PI intercalated in the DNA, and the analysis is carried out using the EXPO32 ADC software (Applied Cytometry Systems, V 1.1 build 207).

3) Western Blotting:

BRIN-BD11 cells are seeded at a density of $0.5 \times 10^5$ cells/ml in T25 flasks for 24 hours. As indicated above, the complete medium is then replaced by an equivalent lacking FCS but containing the lipid reagents of interest. After 6 hours of incubation, total protein is extracted using lysis buffer (20 mM Tris, 150 mM NaCl, 1 mM EDTA and 1% (v/v) Triton-X) containing protease and phosphatase inhibitors. These proteins are then subjected to electrophoresis on a 12% NuPAGE® Novex® Bis-Tris Gels (Invitrogen) acrylamide gel before being transferred to a PVDF membrane and then probed using anti-phospho-eIF2α antibody (Cell Signaling New England Biolabs) diluted to 1/1000. Next, the membranes are stripped with the buffer Re-Blot Plus-Strong (Millipore) before being probed a second time with anti-total eIF2α antibodies (Cell Signaling, New England Biolabs) diluted to 1/1000. The densitometric analysis of the relative abundance of phosphorylated or non-phosphorylated forms of eIF2α protein is carried out with the Fluor-S MultiImager analysis system combined with the Quantity One software (Bio-Rad UK Ltd).

D/ Monitoring of Insulin Maturation (See FIG. 9)

In the manner of that described above for the lipointoxication of BRIN-BD11 cells, the MIN6 cell line is grown in complete DMEM-High Glucose medium (6 mM), supplemented with 10% (v/v) fetal calf serum (FCS), 15 mM HEPES, 100 U/ml penicillin and 100 µg/ml streptomycin, and lipointoxication is induced by exposure to 400 µM palmitic acid, coupled to BSA (0.92% (w/v) final), for 48 hours, with or without the addition of the compound of interest (see Boslem et al., 2011). The cells are then collected and a Western blot is carried out as indicated above, using anti-insulin antibodies in order to follow the maturation of proinsulin to insulin.

E/ Test of Calcium Mobilization (See FIG. 7)

The human epithelial cell line CFBE is grown on glass bottom dishes in MEM+GlutaMAX™-1 medium (aMEM; Invitrogen) supplemented with 10% fetal calf serum (FCS), 100 IU/ml penicillin, 100 µg/ml streptomycin and 0.5 µg/ml puromycin. The cells are first loaded with 3 µM fluorescent calcium probe, Fluo-4-acetoxymethyl ester (FluoProbes®), for 20 minutes at room temperature. Calcium mobilization is then recorded by the acquisition of changes in fluorescence intensity, for an area of interest, by means of a Zeiss Axio Observer Z1 inverted microscope, for 250 ms sequences of laser stimulation, for 4 minutes. The collected data are then interpreted using the Carl Zeiss AxioVision Release 4.8.2 software and the associated physiological acquisition module. Finally, the intensity profiles are normalized by dividing the intensity at each pixel at time t (F) by the fluorescence intensity at said pixel prior to stimulation ($F_0$). The images $((F-F_0)/F_0)$ thus obtained make it possible to obtain a profile of calcium intensity/mobilization over the entire recording (see Vachel et al., 2013).

F/ Restoration of Growth

1) Compound Screening:

Following the induction of SFA lipointoxication (for hem1Δ grown on solid medium) 5 µl drops of solutions of the various compounds at 10 mM in dimethylsulfoxide (DMSO) or ethanol (EtOH) are deposited on the surface of the agar. The ability of a compound to counter the arrest of lipid-induced cell growth is estimated by the appearance of a halo of hem1Δ colonies at the site of the deposition of said compound after 3 days of culture at 28° C. (see Deguil et al., 2011).

2) Proliferation Kinetics:

Jointly with the induction of SFA lipointoxication (for hem1Δ in liquid medium), the various compounds are added to the cultures at an initial concentration of 200 µM. Proliferation is monitored by spectrometric measurement of cell density, at regular time intervals (every hour over the duration of the observation). At a wavelength of 600 nm, one optical density unit ($OD_{600}$ nm) corresponds to $2 \times 10^7$ cells/ml.

G/ Toxicity Test

In parallel, wild-type (WT) and quadruple mutant (QM) strains are grown, under aerobic conditions, with shaking and at 28° C., in liquid YPG medium before seeding 3500 cells per $cm^2$ of YPG+2% agar (w/v). Following this transfer to solid medium, 1 µl drops of 1, 10 and 100 mM solutions of the various compounds in DMSO or EtOH are deposited on the agar surface. Separately, DMSO and EtOH are also deposited in order to evaluate the intrinsic toxicity of these two solvents. After 3 days of culture at 28° C., the toxicity of the compounds tested is evaluated by comparing the growth inhibition halo diameters obtained for the depositions of pure solvent with those of the depositions of the various concentrations of the compounds tested. Unlike the WT strain, the QM strain is incapable of buffering excess exogenous oleic acid in the form of neutral lipids (triglycerides (TG) or esterified sterols (ES)) in lipid droplets. Thus, in the case of an absence of toxicity with respect to the WT strain, the observation of toxicity of a compound with respect to the QM strain indicates that this compound is perceived as a source of free fatty acid by yeasts.

H/ Total Lipid Extraction

The hem1Δ strain is grown in liquid medium ($YPG^A$, $YPG^+$, or $YPG^+$+200 µM compound to be tested) under aerobic conditions, with shaking and at 28° C. for 7 hours, from an initial cell concentration of $2 \times 10^6$ cells/ml. At the conclusion of the culture, $10^8$ cells are collected in order to carry out a total lipid extraction. After having suspended the cells in 1 ml of distilled water at 4° C., 500 µl of glass beads (Ø 0.6 mm) are added and the whole then undergoes 3 sequences of 20 seconds at 5000 rpm in a shaker (the tubes are kept on ice between each of the 3 sequences). The cell lysate then obtained, supplemented with bead-washing solution (1 ml), is then transferred to a 40 ml glass tube (Corex™) before carrying out the lipid extraction using a 2:1 (v/v) methanol:chloroform ratio. First, 6 ml of methanol is added and the whole is vortexed for 30 seconds and then incubated for 15 minutes at 65° C. Once the mixture cools to room temperature, 3 ml of chloroform is added and then the whole is vortexed again for 30 seconds before allowing the extraction to proceed for 16 hours. Later, the sample is centrifuged for 12 minutes at 10000 g before transferring the supernatant to a new Corex™ tube. After adding 2 ml of chloroform and then 4 ml of distilled water, the whole is vortexed for 30 seconds and then centrifuged for 8 minutes at 3000 g. After removing the resulting upper phase, the lower organic phase is collected in a glass hemolysis tube. Finally, the solvent is evaporated under a stream of nitrogen at 80° C. in order to obtain the total cellular lipid samples.

I/ Phospholipid Purification and Mass Spectrometry Analysis

The total cellular lipid samples are resuspended in 1 ml of dichloromethane while being vortexed for 30 seconds. The whole is deposited on a silica column (BOND ELUT-SI, 100 mg 1 ml) preconditioned successively with 3 ml of methanol and then 2 ml of dichloromethane. The fraction retained by the column is then washed successively with 2 ml of dichloromethane and then 3 ml of acetone. Finally, 2 ml of a 50:45:5 (v/v/v) chloroform/methanol/water mixture is deposited on the column and the phospholipids thus eluted are collected in a glass hemolysis tube. The solvent is evaporated under nitrogen at 80° C. in order to obtain the cellular phospholipid samples.

Once resuspended in 100 µl of the mixture Mix⁻ (2:1:1 (v/v/v) isopropanol/acetonitrile/water+1% (v/v) triethylamine) or the mixture Mix⁺ (2:1:1 (v/v/v) isopropanol/acetonitrile/water+1% (v/v) formic acid), the samples are analyzed by electrospray ionization mass spectrometry (ESI-MS) in negative or positive mode, respectively, and the results obtained are used to analyze the fatty acid content of the various phospholipid species.

J/ Test of UPR Triggering

The hem1Δ strain transformed by the plasmid pPW344 [2µ URA3 4×UPRE-lacZ (Patil et al., 2004)] is grown in liquid medium (YPG⁴, YPG, or YPG+200 µM compound to be tested), under aerobic conditions, with shaking at 28° C. for 7 hours, from an initial cell concentration of $2 \times 10^6$ cells/ml. At the conclusion of the culture, $10^8$ cells are collected in order to quantify the β-galactosidase (β-gal) activity resulting from the expression of the lacZ transgene (in the case of UPR activation). First, the cells are resuspended in 1.5 ml of Z-buffer (60 mM $Na_2HPO_4$, 40 mM $NaH_2PO_4$, 10 mM KCl, 1 mM $MgSO_4$ and 50 mM β-mercaptoethanol; solution at pH 7) and then 1/15 of this suspension is used to carry out an $OD_{600\ nm}$ measurement. Second, the suspension is supplemented with 100 µl of 0.1% (v/v) sodium dodecyl sulfate (SDS) and 200 µl of chloroform and then vortexed in two successive 30-second sequences. After decanting, 400 µl (volume V) of the solution thus obtained is transferred to a glass hemolysis tube and then supplemented with 600 µl of Z-buffer. Two hundred microliters of the substrate ortho-nitrophenyl-β-galactoside (ONPG), at 4 mg/ml in Z-buffer, is then added before the whole is homogenized with a vortex and then incubated in a 30° C. water bath in order to initiate the reaction. When the whole has a light yellow tint, the reaction is quenched (at time t), at room temperature, by adding 500 µl of 1 M $Na_2CO_3$. Finally, after having centrifuged the samples for 5 minutes at 800 g and then collected the supernatants in new glass hemolysis tubes, the reaction products (o-nitrophenol) and cell debris are assayed by spectrometry at wavelengths of 420 nm and 550 nm, respectively. For each sample, β-gal activity (U) is calculated using the formula $U=(1000\times[OD_{420\ nm}-(1.75\times OD_{550\ nm})])/(t\times V\times OD_{600\ nm})$, expressed in arbitrary units.

REFERENCES

Alkhateeb H, Chabowski A, Glatz J F C, Luiken J F P, Bonen A (2007) Two phases of palmitate-induced insulin resistance in skeletal muscle: impaired GLUT4 translocation is followed by a reduced GLUT4 intrinsic activity. *American Journal of Physiology—Endocrinology And Metabolism* 293: E783-E793.

Bigay J, Casella J F, Drin G, Mesmin B, Antonny B. ArfGAP1 responds to membrane curvature through the folding of a lipid packing sensor motif. EMBO J. 2005 Jul. 6; 24(13):2244-53.

Boslem E, MacIntosh G, Preston A M, Bartley C, Busch A K, Fuller M, Laybutt D R, Meikle P J, Biden T J. A lipidomic screen of palmitate-treated MIN6 β-cells links sphingolipid metabolites with endoplasmic reticulum (ER) stress and impaired protein trafficking. Biochem J. 2011 Apr. 1; 435(1):267-76.

Butler A E, Janson J, Bonner-Weir S, Ritzel R, Rizza R A, Butler P C. (2003) β-Cell Deficit and Increased β-Cell Apoptosis in Humans With Type 2 Diabetes. Vol. 52, pp. 102-110.

Cnop M, Hannaert J C, Hoorens A, Eizirik D L, Pipeleers D G (2001) Inverse Relationship Between Cytotoxicity of Free Fatty Acids in Pancreatic Islet Cells and Cellular Triglyceride Accumulation. Diabetes 50: 1771-1777.

Cunha D A, Hekerman P, Ladriere L, Bazarra-Castro A, Ortis F, Wakeham M C, Moore F, Rasschaert J, Cardozo A K, Bellomo E, Overbergh L, Mathieu C, Lupi R, Hai T, Herchuelz A, Marchetti P, Rutter G A, Eizirik D L, Cnop M. (2008) Initiation and execution of lipotoxic ER stress in pancreatic {beta}-cells. Vol. 121, pp. 2308-2318.

Deguil J, Pineau L, Rowland Snyder E C, Dupont S, Beney L, Gil A, Frapper G, Ferreira T (2011) Modulation of Lipid-Induced ER Stress by Fatty Acid Shape. *Traffic* 12: 349-362.

Dhayal S, Morgan N G (2011) Structure-activity relationships influencing lipid-induced changes in eIF2alpha phosphorylation and cell viability in BRIN-BD11 cells. *FEBS Lett* 585: 2243-2248.

Diakogiannaki E, Morgan N G. (2008) Differential regulation of the ER stress response by long-chain fatty acids in the pancreatic β-cell. Vol. 036, pp. 959-962.

Diakogiannaki E, Welters H J, Morgan N G. (2008) Differential regulation of the endoplasmic reticulum stress response in pancreatic {beta}-cells exposed to long-chain saturated and monounsaturated fatty acids. Vol. 197, pp. 553-563.

Egnatchik R A, Leamy A K, Jacobson D A, Shiota M, Young J D. ER calcium release promotes mitochondrial dysfunction and hepatic cell lipotoxicity in response to palmitate overload. Mol Metab. 2014 May 22; 3(5):544-53.

Guo W, Wong S, Xie W, Lei T, Luo Z. (2007) Palmitate modulates intracellular signaling, induces endoplasmic reticulum stress, and causes apoptosis in mouse 3T3-L1 and rat primary preadipocytes. Vol. 293, pp. E576-586.

Iwasaki Y, Saito O, Tanabe M, Inayoshi K, Kobata K, Uno S, Morita A, Watanabe T. Monoacylglycerols activate capsaicin receptor, TRPV1. Lipids. 2008 June; 43(6):471-83.

Kato T, Shimano H, Yamamoto T, Ishikawa M, Kumadaki S, Matsuzaka T, Nakagawa Y, Yahagi N, Nakakuki M, Hasty A H, Takeuchi Y, Kobayashi K, Takahashi A, Yatoh S, Suzuki H, Sone H, Yamada N. (2008) Palmitate Impairs and Eicosapentaenoate Restores Insulin Secretion Through Regulation of SREBP-1c in Pancreatic Islets. Vol. 57, pp. 2382-2392.

Katsoulieris E, Mabley J G, Samai M, Green I C, Chatterjee P K (2009) [alpha]-Linolenic acid protects renal cells against palmitic acid lipotoxicity via inhibition of endoplasmic reticulum stress. *European Journal of Pharmacology* 623: 107-112.

Kincaid M M, Cooper A A (2007) ERADicate E R Stress or Die Trying. *Antioxid Redox Signal*.

Kohlwein S D, Petschnigg J (2007) Lipid-induced cell dysfunction and cell death: lessons from yeast. *Current hypertension reports* 9: 455-461.

Laybutt D R, Preston A M, Akerfeldt M C, Kench J G, Busch A K, Biankin A V, Biden T J (2007) Endoplasmic reticulum stress contributes to beta cell apoptosis in type 2 diabetes. *Diabetologia* 50: 752-763.

Listenberger L L, Han X, Lewis S E, Cases S, Farese R V, et al. (2003) Triglyceride accumulation protects against fatty acid-induced lipotoxicity. PNAS 100: 3077-3082.

Martin A C, Cooper D M. Capacitative and 1-oleyl-2-acetyl-sn-glycerol-activated Ca(2+) entry distinguished using adenylyl cyclase type 8. Mol Pharmacol. 2006 August; 70(2):769-77.

Patil C K, Li H, Walter P. Gcn4p and novel upstream activating sequences regulate targets of the unfolded protein response. PLoS Biol. 2004 August; 2(8):E246.

Payet L A, Pineau L, Snyder E C, Colas J, Moussa A, Vannier B, Bigay J, Clarhaut J, Becq F, Berjeaud J M, Vandebrouck C, Ferreira T. Saturated fatty acids alter the late secretory pathway by modulating membrane properties. Traffic. 2013 Sep. 6.

Petschnigg J, Moe O W, Stagljar I (2011) Using yeast as a model to study membrane proteins. *Current opinion in nephrology and hypertension* 20: 425-432.

Petschnigg J, Wolinski H, Kolb D, Zellnig Gn, Kurat C F, Natter K, Kohlwein S D (2009) Good Fat, Essential Cellular Requirements for Triacylglycerol Synthesis to Maintain Membrane Homeostasis in Yeast. *J Biol Chem* 284: 30981-30993.

Pineau L, Bonifait L, Berjeaud J-M, Alimardani-Theuil P, Berges T, Ferreira T (2008) A Lipid-mediated Quality Control Process in the Golgi Apparatus in Yeast. *Mol Biol Cell* 19: 807-821.

Pineau L, Colas J, Dupont S, Beney L, Fleurat-Lessard P, Berjeaud J M, Berges T, Ferreira T (2009) Lipid-Induced ER Stress: Synergistic Effects of Sterols and Saturated Fatty Acids. *Traffic*.

Pineau L, Ferreira T (2010) Lipid-induced ER stress in yeast and 3 cells: parallel trails to a common fate. *FEMS Yeast Research*.

Poon P P, Nothwehr S F, Singer R A, Johnston G C. The Gcs1 and Age2 ArfGAP proteins provide overlapping essential function for transport from the yeast trans-Golgi network. J Cell Biol. 2001 Dec. 24; 155(7):1239-50.

Robinson M, Poon P P, Schindler C, Murray L E, Kama R, Gabriely G, Singer R A, Spang A, Johnston G C, Gerst J E. The Gcs1 Arf-GAP mediates Snc1,2 v-SNARE retrieval to the Golgi in yeast. Mol Biol Cell. 2006 April; 17(4): 1845-58.

Schneider M F, Marsh D, Jahn W, Kloesgen B, Heimburg T. Network formation of lipid membranes: triggering structural transitions by chain melting. Proc Natl Acad Sci USA. 1999 Dec. 7; 96(25):14312-7.

Stein D T, Stevenson B E, Chester M W, Basit M, Daniels M B, Turley S D, McGarry J D (1997) The insulinotropic potency of fatty acids is influenced profoundly by their chain length and degree of saturation. *The Journal of Clinical Investigation* 100: 398-403.

Stutzmann G E, Mattson M P. Endoplasmic reticulum Ca(2+) handling in excitable cells in health and disease. Pharmacol Rev. 2011 September; 63(3):700-27.

Wei Y, Wang D, Topczewski F, Pagliassotti M J. (2006) Saturated fatty acids induce endoplasmic reticulum stress and apoptosis independently of ceramide in liver cells. Vol. 291, pp. E275-281.

Zhang K, Kaufman R J. (2006) The unfolded protein response: A stress signaling pathway critical for health and disease. Vol. 66, pp. S102-109.

Vachel L, Norez C, Becq F, Vandebrouck C. Effect of VX-770 (ivacaftor) and OAG on Ca2+ influx and CFTR activity in G551D and F508del-CFTR expressing cells. J. Cyst. Fibros. 2013 December; 12(6):584-91.

The invention claimed is:

1. A method for symptomatically treating, or for delaying or slowing progression of dyslipidemia linked to the excess presence of fatty acids in biological membranes of a human subject suffering from type 2 diabetes mellitus or metabolic syndrome comprising administering to the subject a derivative of unsaturated fatty acid or fatty acid amide compound consisting of an effective amount of mannide monooleate, 3-hydroxy-2,2-bis(hydroxymethyl)propyl oleate or N,N-diethanololeamide.

2. The method according to claim 1, wherein the method is characterized in that dyslipidemia is responsible for the lipointoxication, dysfunction or apoptosis of non-adipocyte cells by decreasing or suppressing the fluidity of plasma membranes and/or organelle membranes of said non-adipocyte cells.

3. The method according to claim 1, wherein the method is characterized in that the compound is nontoxic to cells unable to synthesize neutral lipids.

4. The method according to claim 1, wherein the dyslipidemia is associated with the presence of metabolic syndrome.

5. The method according to claim 4, wherein or symptomatically treats or reduces at least one symptom of metabolic syndrome said method symptomatically treats or reduces at least one symptom of metabolic syndrome selected from the group consisting of insulin resistance, hyperglycemia, hypercholesterolemia, hypertriglyceridemia, hypertension, heart failure and hepatic steatosis.

6. The method according to claim 1, wherein the method comprises administering said compound in combination with a biguanide, glitazone, sulfonamide-based hypoglycemic, glinide, DPP-4 inhibitor, incretin mimetic or α-glucosidase inhibitor.

7. The method according to claim 1, wherein said compound i) does not allow the production of diunsaturated phospholipids in the membrane of the cells in the subject, ii) does not constitute a source of oleic acid for the cells in the subject and iii) does not induce intracellular calcium mobilization and/or is not degraded by lipases.

* * * * *

UNITED STATES PATENT AND TRADEMARK OFFICE
CERTIFICATE OF CORRECTION

PATENT NO. : 10,231,985 B2
APPLICATION NO. : 15/028139
DATED : March 19, 2019
INVENTOR(S) : Miroslava Spanova et al.

It is certified that error appears in the above-identified patent and that said Letters Patent is hereby corrected as shown below:

In the Specification

Column 10,
Lines 3-4, "encoding 0–galactosidase" should read --encoding β–galactosidase--.

Column 21,
Line 6, "addition (0)" should read --addition (ø)--.
Line 56, "conditions (0)" should read --conditions (Ø)--.

Column 22,
Line 43, "6–aminolevulinic acid" should read --δ–aminolevulinic acid--.

Column 23,
Line 66, "(aMEM;" should read --(αMEM;--.

Column 24,
Line 35, "unit ($OD_{600}$ nm)" should read --unit ($OD_{600\ nm}$)--.

In the Claims

Column 28,
Lines 46-50, "5. The method according to claim 4, wherein or symptomatically treats or reduces at least one symptom of metabolic syndrome said method symptomatically treats or reduces at least one symptom of metabolic syndrome selected from the group consisting of insulin resistance" should read --5. The method according to claim 4, wherein said method symptomatically treats or reduces at least one symptom of metabolic syndrome selected from the group consisting of insulin resistance--.

Signed and Sealed this
Twenty-fourth Day of September, 2019

Andrei Iancu
*Director of the United States Patent and Trademark Office*